United States Patent [19]
Fujimoto

[11] Patent Number: 5,588,434
[45] Date of Patent: Dec. 31, 1996

[54] ULTRASONIC DIAGNOSTIC APPARATUS PRESENTING CLOSELY CORRELATED ULTRASONIC IMAGE

[75] Inventor: Hiroshi Fujimoto, Hachioji, Japan

[73] Assignee: Olympus Optical Co., Ltd., Tokyo, Japan

[21] Appl. No.: 537,281

[22] Filed: Sep. 29, 1995

[30] Foreign Application Priority Data

Oct. 3, 1994 [JP] Japan ................................ 6-239247
Sep. 20, 1995 [JP] Japan ................................ 7-241958

[51] Int. Cl.$^6$ ................................................. A61B 8/00
[52] U.S. Cl. ................................................. 128/660.07
[58] Field of Search ..................... 128/660.04, 660.07, 128/660.08, 660.09, 661.01, 661.04

[56] References Cited

U.S. PATENT DOCUMENTS 4,846,188  7/1989  Yoshioka .
5,099,847  5/1992  Powers et al. ...................... 128/660.07
5,152,290  10/1992  Freeland ............................. 128/660.07

FOREIGN PATENT DOCUMENTS 4-343839  11/1992  Japan .

Primary Examiner—George Manuel
Attorney, Agent, or Firm—Armstrong, Westerman, Hattori, McLeland & Naughton

[57] ABSTRACT

The ultrasonic wave generated by an ultrasonic transducer mounted at the end of an insert assembly scans a region of scanning. Ultrasonic echo is received by the transducer. A video memory stores sequentially video data of a plurality of video frames or scanning durations. With a freeze operation is commanded, the degree of coincidence between data obtained at the start of scanning and at the end of the scanning is calculated, or the degree of coincidence between two identical sounding lines but with one scanning duration apart in time therebetween is calculated. The video of highest coincidence is displayed as a still video.

29 Claims, 21 Drawing Sheets

NORMAL IMAGE

DISTORTED AT 3 O'CLOCK POSITION

DISTORTED IMAGE

DIRECTION OF SCANNING

512TH BEAM
1ST BEAM
2ND BEAM

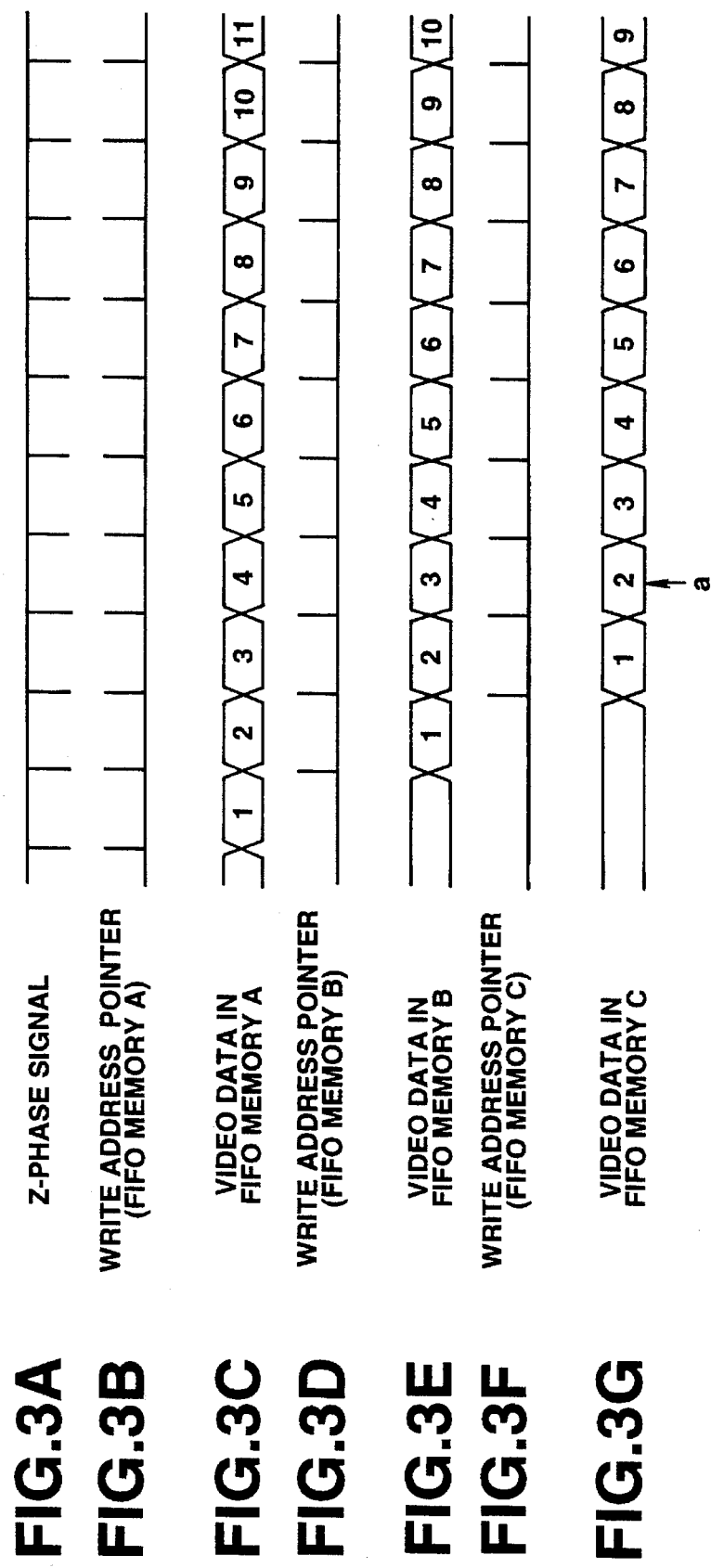

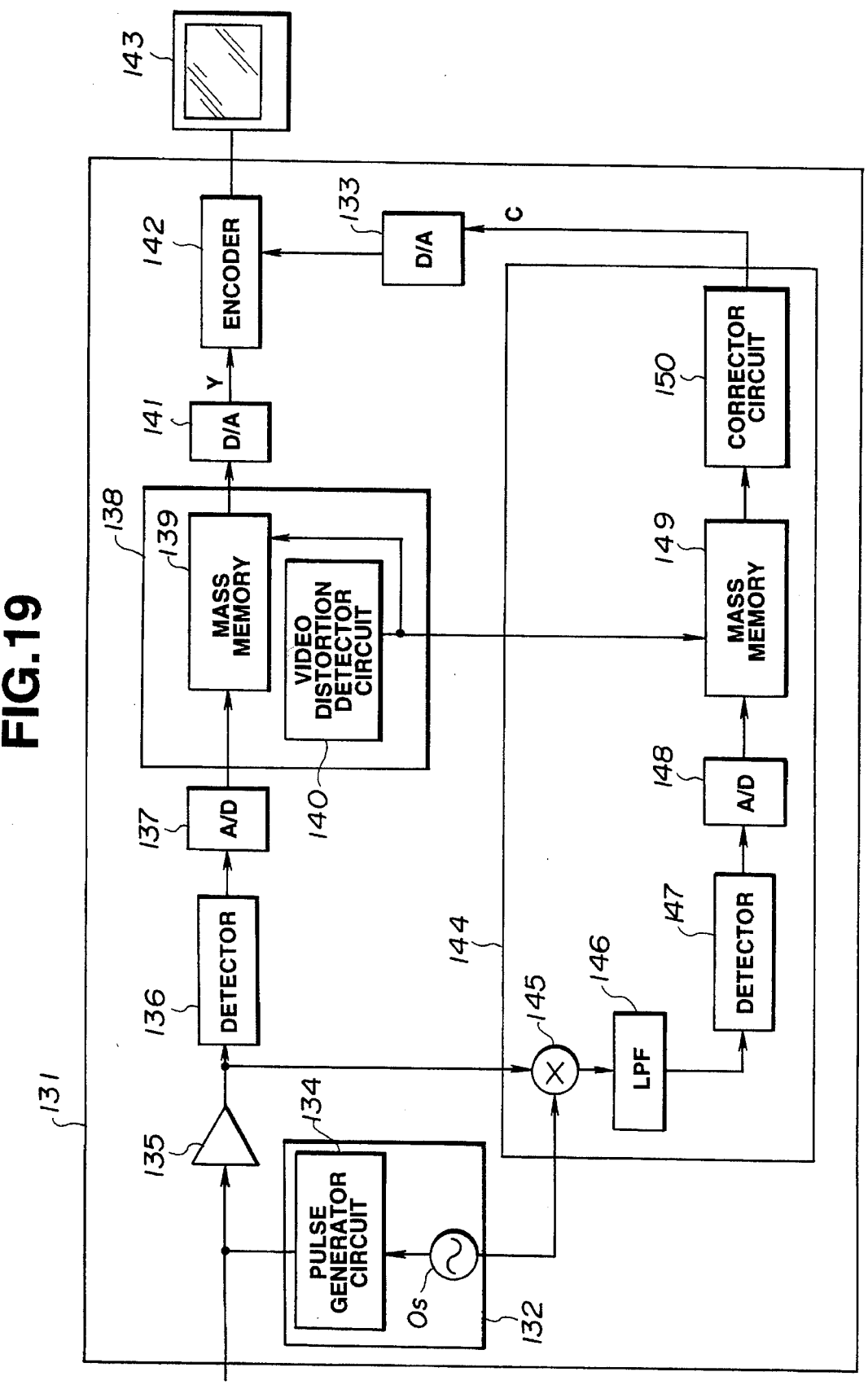

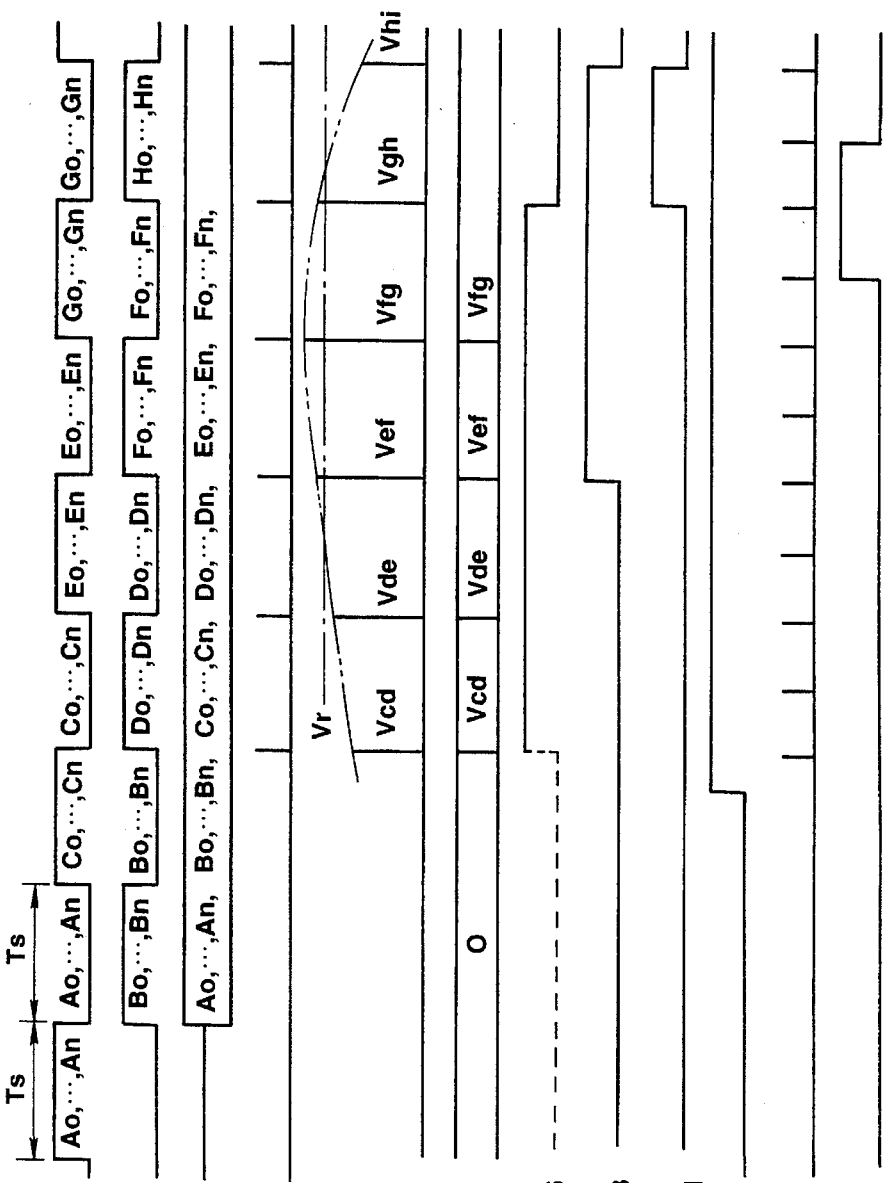

ULTRASONIC DIAGNOSTIC APPARATUS PRESENTING CLOSELY CORRELATED ULTRASONIC IMAGE

BACKGROUND OF THE INVENTION

1. Field of the Invention

The present invention relates to an ultrasonic diagnostic apparatus that transmits ultrasonic wave to a living organ and receives the echo from it, detects the degree of coincidence between two scanning data and acquires the least moving ultrasonic image when the organ moves.

2. Description of the Related Art

A known ultrasonic diagnostic apparatus transmits ultrasonic wave to a living tissue and then produces a tomographic image or video of the living tissue based on the echo signal returned from it. Now in widespread use in this field today is such an ultrasonic diagnostic apparatus that uses, as a transducer for transmitting ultrasonic wave to and receiving the echo signal from a target region, a mechanical scanning ultrasonic endoscope having an ultrasonic transducer on its end or an ultrasonic probe having no optical system such as image guide, which is inserted into a body cavity to diagnose the target region in an endoscopic manner.

Such an ultrasonic diagnostic apparatus having an ultrasonic endoscope allows its ultrasonic transducer to mechanically scan. In the course of diagnosing process, the living tissue may be agitated (for example, when the body of a subject moves), or an insertion portion of the endoscope may be shaken particularly when it is soft tissue. Thus, the region of the tissue with which the transducer is contact is also moved, and a resulting tomographic image is substantially distorted.

When a PPI (Plan Position Indicator) scanning, typically employed in many of radar installations, is performed, tomographic images occasionally suffer discontinuity in presentation due to movement of the region to be probed when the body or transducer is agitated. The resulting images are thus distorted and image quality is degraded.

To improve poor quality image, Japanese Patent Application No. 4-343839 has disclosed a monitoring apparatus in which display start position modifier means for ultrasonic image is provided so that the degradation of a tomographic image is prevented by an operator's own operation.

During diagnosing process using an ultrasonic diagnosing apparatus, an operator must use both hands to insert an ultrasonic endoscope or ultrasonic probe into the body cavity. The above disclosed method in which a degraded image is corrected by manipulating the display start position modifier means is neither easy nor practicable. Furthermore, in the above disclosure, if degradation of an image due to agitated body or transducer (ultrasonic transducer) affects a plurality of frames that started before stopping of scanning operation, correction action to the image will not work.

U.S. Pat. No. 4,846,188 has disclosed an ultrasonic diagnosing apparatus in which heart beat interval is divided by a number into a plurality of segments, and scanning sector is divided by the same number. An ultrasonic image is obtained in synchronism with the segments of the heart beat intervals. This technique, however, is not applicable to the case where image acquisition requires frame rate far faster than the heart rate.

The human heart beats about once a second, while the frame rate of the typical ultrasonic image ranges from 1/30 second to 1/10 second. The frame rate on the order of the human heart rate is only applicable to the special case where the imaging acquisition requirement is slow. Furthermore, the heart beat varies in response to a change in its surrounding situation. The above disclosed technique has thus difficulty with ordinary ultrasonic imaging application.

SUMMARY OF THE INVENTION

It is an object of the present invention to provide an ultrasonic diagnosing apparatus which offers a substantially less degraded image without the need for correction action by an operator even when the image is degraded due to the movement of a body to be diagnosed or of the transducer of the apparatus.

It is another object of the present invention to provide an ultrasonic diagnosing apparatus which offers a high-quality still image within a short time of period even when the image is degraded due to the movement of a body to be diagnosed or of the transducer of the apparatus.

The ultrasonic diagnosing apparatus according to the present invention comprises:

an ultrasonic transducer;

ultrasonic generator means that feeds a driving signal to the ultrasonic transducer to generate ultrasonic wave;

scanning means for causing the ultrasonic wave generated by the ultrasonic transducer to scan a predetermined scanning sector for a predetermined scanning duration;

video data memory means for storing returned signals, which are received and electro-acoustically converted by the transducer, in a plurality of video frames of video data obtained over a plurality of predetermined scanning durations, video frame by video frame, each video frame corresponding to the scanning sector;

video distortion detector means for detecting the degree of distortion in the video in each of the video frames stored in the video data memory means;

video selector control means for performing selection control so that the video data memory means outputs selectively the video of a video frame that is found to suffer less degree of distortion based on the degree of distortion detected by the video distortion detector means; and video display means for presenting the video of the Video frame selected by the video selector control means, whereby the video distortion detector means determines the degree of distortion of the plurality of images stored and the video selector control means presents a less distorted video based on the result of distortion determination.

BRIEF DESCRIPTION OF THE DRAWINGS

FIG. 1 through FIG. 7L are related to the ultrasonic diagnosing apparatus according to embodiment 1 of the present invention.

FIG. 1 is a block diagram showing generally the construction of the ultrasonic diagnosing apparatus.

FIGS. 3A through 3G are timing diagrams showing the operation of the buffer memory block that stores video data of a plurality of video frames.

FIG. 4 is a flow diagram showing the process of still video presentation.

FIG. 5 is an explanatory view showing each line of video data obtained at each transmission of ultrasonic wave in scanning operation.

FIG. 6 is a block diagram showing the selector disposed in the buffer memory block for selecting less distorted video data.

FIG. 7A through 7L are timing diagrams showing the operation of the selector of FIG. 6.

FIG. 8 is a block diagram showing the construction of the ultrasonic diagnosing apparatus according to the embodiment 2 of the present invention.

FIG. 9 is a plan view showing the panel layout of the keyboard for video correction and cine-loop correction.

FIGS. 11 through 12E are related to embodiment 4 of the present invention.

FIG. 11 is a block diagram showing the major portion of the ultrasonic diagnosing apparatus according to the embodiment 4.

FIG. 12A through 12E are timing diagrams showing the operation of the ultrasonic diagnosing apparatus of FIG. 11.

FIG. 15 through FIG. 18B are related to embodiment 7 of the present invention.

FIG. 15 is a perspective view showing the end portion of the electronic scanning endoscope of the embodiment 7.

FIG. 16 is a block diagram showing the ultrasonic diagnostic apparatus according to the embodiment 7.

FIG. 17 is a block diagram of the video memory block of the ultrasonic diagnostic apparatus.

FIGS. 18A and 18B show respectively a sector scanning image and a 360° full-circle scanning image.

FIG. 19 is a block diagram showing the major portion of the ultrasonic control unit according to embodiment 8 of the present invention.

FIG. 20 is a block diagram showing the major portion of the ultrasonic control unit according to the embodiment 9 of the present invention.

FIGS. 21A through 21C are timing diagrams showing the operation of the ultrasonic control unit.

FIG. 22 is an explanatory view showing the affected part of a subject scanned by ultrasonic wave.

FIGS. 24 through 25B are related to embodiment 11 of the present invention.

FIG. 24 is a block diagram showing generally the ultrasonic control unit according the embodiment 11.

FIGS. 25A and 25B diagrammatically show, respectively one image that suffers a relative movement between the affected part of the subject and an ultrasonic treatment endoscope and the other one that suffers not such movement.

FIGS. 26 through 27L are related to embodiment 12 of the present invention.

FIG. 26 is a block diagram showing generally the ultrasonic diagnosing apparatus according to the embodiment 12 of the present invention.

FIGS. 27A through 27L are timing diagrams showing the operation of the ultrasonic diagnosing apparatus.

DETAILED DESCRIPTION OF THE PREFERRED EMBODIMENTS

Figure 1:
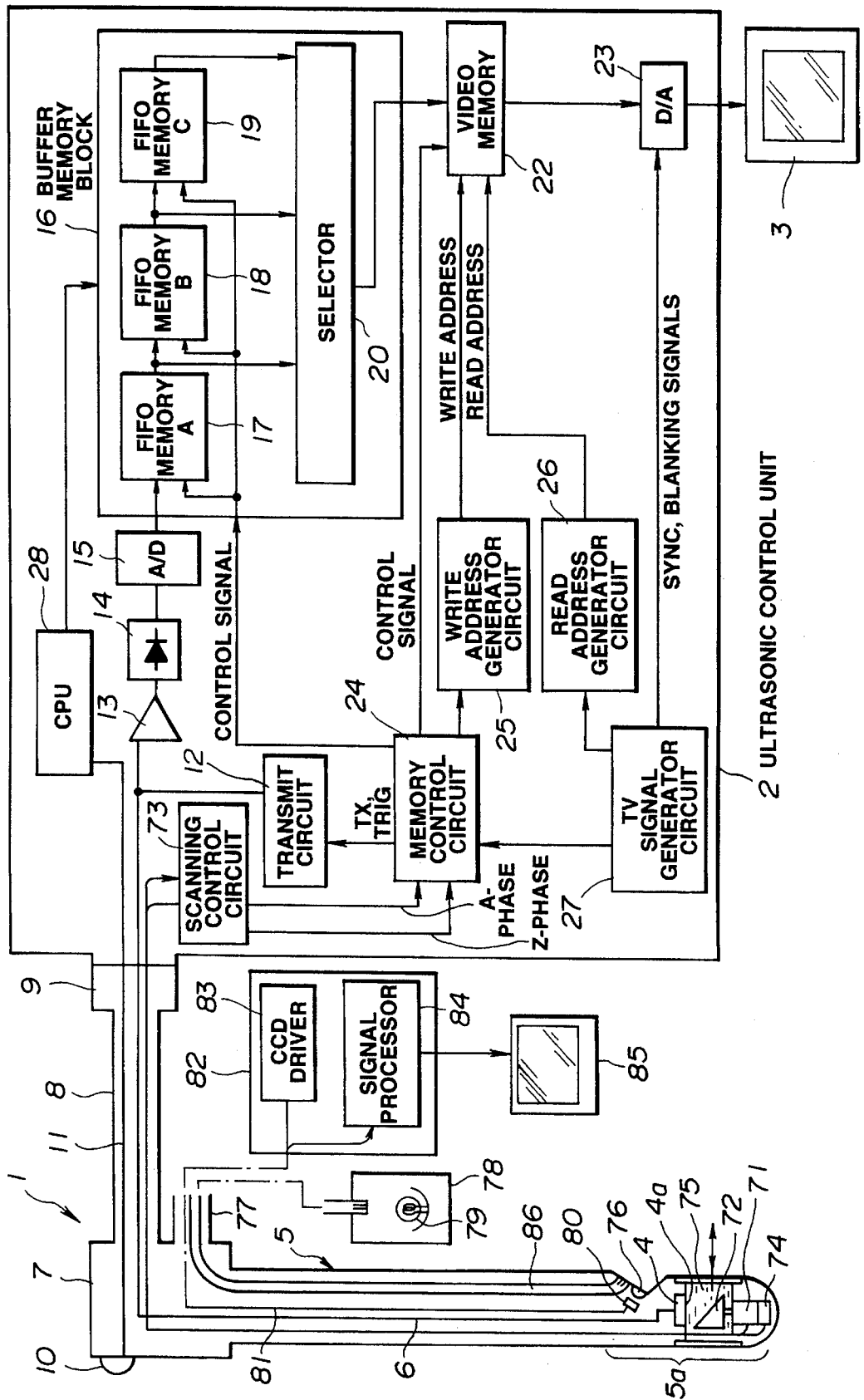

Referring now to the drawings, the embodiments of the present invention are discussed. As shown in FIG. 1, the ultrasonic diagnosing apparatus according to the embodiment 1 of the present invention comprises an ultrasonic endoscope 1 with a guide channel, which is inserted into the body of a subject to acquire the image of the tissue of the subject for treatment by transmitting ultrasonic wave and receiving reflected ultrasonic wave, an ultrasonic control unit 2 connected to the ultrasonic endoscope 1 for producing an image from the acquired ultrasonic signal, and a monitor 3 for presenting the image derived from the ultrasonic control unit 2.

The ultrasonic endoscope 1 electro-acoustically converts a high-tension pulse signal that is fed by the ultrasonic control unit 2, transmits sounding ultrasonic wave toward the tissue of the subject and receives the ultrasonic wave returned from it. The ultrasonic endoscope 1 is equipped with one or a plurality of ultrasonic transducers 4.

The ultrasonic transducer 4 is arranged so that the plane of its transmit/receive surface 4a is perpendicular to the axis of the insert assembly 5 of the ultrasonic endoscope 1 in the end portion 5a of the insert assembly 5. An ultrasonic mirror 72 that is driven by a motor 71 is mounted so that the mirror 72 faces the transmit/receive surface 4a of the transducer 4. The ultrasonic mirror 72 is a cylinder which has a 45° inclined top plane. The top inclined plane of the mirror 72 makes an angle of 45° to the transmit/receive surface 4a of the transducer 4. The axis of rotation of the motor 71 is in parallel with the axis of the insert assembly 5.

The motor 71 is connected to a scanning control circuit 73 in the ultrasonic control unit 2 via a driving cable. Disposed on the axis of rotation of the motor 71 is a rotary encoder 74 that detects the rotational speed of the motor 71. The rotary encoder 74 is connected to the scanning control circuit 73 via the cable. Referring to the output of the rotary encoder 74, the scanning control circuit 73 performs servo control so that the motor 71 rotates at a constant speed. A cylindrical enclosure that surrounds the mirror 72 is formed of a resin that transmits ultrasonic wave. The cylindrical enclosure is filled with a liquid 75 that also transmits ultrasonic wave.

Ultrasonic wave transmitted by the transducer 4 is reflected by the inclined surface of the mirror 72 sideways in the direction perpendicular to the axis of the insert assembly 5. With the mirror 72 rotating, the ultrasonic wave is scanned, namely mechanically scanned.

The ultrasonic transducer 4 is connected to a coaxial cable 6 that is passed through the ultrasonic endoscope 1 to conduct ultrasonic signal. An extension cord 8 that connects the ultrasonic endoscope 1 to the ultrasonic control unit 2 is extended from the handle portion 7 at the proximal end of the insert assembly 5 of the ultrasonic endoscope 1. The extension cord 8 has on its end a connector 9 that mechanically connects the extension cord 8 to the ultrasonic control unit 2.

When the connector 9 is mechanically connected to the ultrasonic control unit 2, the coaxial cable 6 is electrically connected to the circuitry of the ultrasonic control unit 2. The transducer 4 of the ultrasonic endoscope 1 scans in the body of the subject and acquires the tomographic image of the target region. Disposed on the handle portion 7 of the ultrasonic endoscope 1 is a freeze switch 10 for stopping or starting the driving of the transducer 4. The freeze switch 10 is electrically connected to the ultrasonic control unit 2 via a signal line 11.

The end portion 5a is provided with illumination and viewing means. The insert assembly 5 has a V-shaped cutout slightly way back from the mounting position of the ultrasonic transducer 5. The V-shaped cutout has an illumination window and a viewing window, both looking slantly forwardly. The illumination and viewing windows are provided with the distal end of a light guide 86 and an objective lens 76, respectively. The light guide 86 is passed through a universal cord 77 that is extended from the insert assembly 5 and the handle portion 7. The proximal end of the light guide 86 is detachably connected to a light source 78. Light given off by a lamp 79 in the light source 78 is supplied to the proximal end of the light guide 86. The light guide 86 guides light to its distal end on the illumination window, and from there light is projected slantly forwardly.

The objective lens 76 bears the optical image of an illuminated affected part of a subject as its object at its point of focus. Disposed at the image bearing point is the image pickup surface (photoelectric conversion surface) of CCD 80 as a solid-state image pickup device. CCD 80 thus photoelectrically converts the optical image. CCD 80 is connected to an external video processor 82 via a signal cable 81.

The video processor 82 has a CCD driver 83 and a signal processor circuit 84. The CCD driver 83 feeds a driving signal to the CCD 80 and reads photoelectrically converted signal from it. The photoelectrically converted signal is fed to the signal processor circuit 84, where the signal is processed into a standard video signal which is then displayed on a color monitor.

The ultrasonic control unit 2 comprises a transmit circuit 12 for generating a high-tension pulse signal that causes the ultrasonic transducer 4 to transmit ultrasonic wave, and a preamplifier 13 for receiving and then amplifying an electrical echo signal when the ultrasonic transducer 4 receives the echo or the ultrasonic wave returned from the living tissue of the subject and electro-acoustically converts it into the electrical echo signal. These components are connected to the coaxial cable 6 of the ultrasonic endoscope 1.

Connected to the output of the preamplifier 13 is a detector circuit 14 that detects the envelope of the amplified electrical echo signal. The output of the detector circuit 14 is connected to an A/D converter 15 that analog-to-digital converts its input into a digital signal. The signal detected or demodulated by the detector circuit 14 is input to the A/D converter 15, where the input signal is converted into the digital signal that reflects the strength of ultrasonic echo from the target.

The output of the A/D converter 15 is connected to a buffer memory block 16. The buffer memory block 16 stores the digital data output by the A/D converter 15.

The buffer memory block 16 contains, as video data memory means, a plurality of FIFO memories (three in this embodiment) 17, 18, and 19 for storing a plurality of video frames of ultrasonic image based on the digital data. A selector 20 as video selector control means is provided to selectively switch one from another among the output data of the FIFO memory A 17, FIFO memory B 18 and FIFO memory C 19.

The output of the buffer memory block 16 is connected to a video memory 22 that has read and write capability. The video memory 22 stores data that is once stored and then output by the buffer memory block 16. The output of the video memory 22 is connected to the a D/A converter 23. Data read from the video memory 22 is fed to the D/A converter 23, where the data is digital-to-analog converted into an analog signal that is output as video signal to a monitor 3.

A memory control circuit 24 is provided to control the FIFO memories 17, 18 and 19 and the video memory 22. The memory control circuit 24 outputs control signals to the memories 17, 18, 19 and 22 to control them. Also provided are a write address generator circuit 25 for generating a write address signal for the video memory 22 and a read address generator circuit 26 for generating a read address signal for video memory 22.

The ultrasonic endoscope 1 contains an encoder 74 that detects the motion of the ultrasonic transducer 4 (angle of rotation in this embodiment). The write address signal for the video memory 22 may be generated by the write address generator circuit 25 under the control of the memory control circuit 24, based on an A-phase signal and Z-phase signal (of the encoder 74) provided through a scanning control circuit 73.

The ultrasonic control unit 2 further comprises a TV signal generator circuit 27 for generating synchronizing signals required for presenting a video signal. The read address generator circuit 26 generates the read address signal for the video memory 22, based on the two signals, a horizontal scanning signal (HD signal) and a vertical scanning signal (VD signal) from the TV signal generator circuit 27.

The TV signal generator circuit 27 feeds synchronizing signals (SYNC signal and blanking signal, for example) to the D/A converter 23. The D/A converter 23 produces the video signal in response to these synchronizing signals. Also provided is CPU 28 that controls the buffer memory block 16. The signal line 11 connects the freeze switch 10 to CPU 28.

The operation of the ultrasonic diagnosing apparatus of this embodiment is now discussed. In the discussion that follows, it is assumed that a full-circle scanning is performed to acquire a tomographic image (namely, ultrasonic wave is scanned by 360° around the axis of the insert assembly 5 of the endoscope 1).

Ultrasonic wave transmitted from the ultrasonic transducer 4 of the ultrasonic endoscope 1 is scanned by the mirror 72 that is rotated by the motor 71. The encoder 74, mounted on the motor 71, outputs, via the scanning control circuit 73, an angle of rotation signal (A-phase signal, for example) indicative of the angle of rotation of the ultrasonic transducer 4 and a reference angular position signal (Z-phase signal, for example) indicative of the initial angular position of the ultrasonic transducer 4. The A-phase and Z-phase signals are fed to the memory control circuit 24 in the ultrasonic control unit 2. The memory control circuit 24 outputs a TX TRIG signal in synchronism with the A-phase signal. The TX TRIG signal is fed to the transmit circuit 12. The transmit circuit 12 generates the high-tension pulse signal in synchronism with the TX TRIG signal. The high-tension pulse signal generated in the transmit circuit 12 is fed to the ultrasonic transducer 4 via the coaxial cable 6. In response to the high-tension pulse signal, the transducer 4 transmits ultrasonic wave.

Ultrasonic wave transmitted by the ultrasonic transducer 4 is projected to the living tissue of interest via the mirror 72 and part of it is returned from there. The returned ultrasonic wave, so-called ultrasonic echo, is received by the ultrasonic transducer 4, which in turn converts the ultrasonic echo into an electrical echo signal. The electrical echo signal is conducted via the coaxial cable 6 to the preamplifier 13 in the ultrasonic control unit 2. The preamplifier 13 amplifies the electrical echo signal, which is then demodulated by the detector circuit 14. The output signal of the detector circuit 14 is a voltage signal that represents the strength of ultrasonic echo returned from the living tissue. The demodulated signal is then converted into digital data (video data representing an ultrasonic tomographic image) by the A/D converter 15, and then temporarily stored in the buffer memory block 16.

The buffer memory block 16 stores a plurality of frames of video data and then selectively outputs the stored video data to the video memory 22 that is connected to the buffer memory block 16.

The video memory 22 may be constructed of a memory having read/write capability (a static RAM, for example). Each address generated by the write address generator circuit 25 and read address generator circuit 26 is a polar coordinates position corresponding to a rectangular coordinates position on a displayed image. By entering this address as the write address and read address to the video memory 22, video data in polar coordinates obtained from scanning operation is converted into rectangular coordinates data which is then displayed on the X-Y monitor 3.

The D/A converter 23 superimposes the synchronizing signals from the TV signal generator circuit 27 onto the video data that is already coordinate converted (from polar to rectangular coordinates) by the video memory 22, and the resulting signal is converted into an analog video signal. The video signal is then fed to the monitor 3, where it is presented as an intensity-modulated, B-display image.

The ultrasonic tomographic image of the region of interest of the subject is presented, and the operator thus monitors the state of the living tissue.

In the ultrasonic endoscope that presents the tomographic image by means of mechanical scanning, the still video presentation may suffer distortion (discontinuity in the image) at 3 o'clock position, for example, when scanning is started at 3 o'clock. This embodiment automatically corrects such a distortion (namely selects the least distorted image). To this end, the least distorted video data among the plurality of video frames stored in the buffer memory block 16 is detected. After a freeze operation, the selected video data is presented.

The buffer memory block 16 has the plurality of FIFO memories (three memories in this embodiment) to store images of the plurality of video frames in succession in time and detect the least distorted image. FIG. 3A through 3G show the operation timing of each of FIFO memories of the buffer memory frame. The timing of the write operation of each of the FIFO memories 17, 18 and 19 is controlled by the memory control circuit 24.

The video data in FIFO memory A 17 is updated each time the Z-phase signal (FIG. 3A) is entered with the write address pointer (FIG. 3B) initialized. The video data (FIG. 3C) written onto FIFO memory A17 is continually updated. The video data once stored in FIFO memory A 17 is sent to the video memory 22 via the selector 20, and then digital-to-analog converted by the D/A converter 23 to be displayed as a motion video.

The video data in FIFO memory B 18 is updated with the write address pointer (FIG. 3D) initialized, but with a delay of a single cycle of the Z-phase signal compared with FIFO memory A 17. Therefore, FIFO memory B 18 stores video data (FIG. 3E), which is delayed by one video frame.

The video data in FIFO memory B 19 is updated with the write address pointer (FIG. 3F) initialized, but with a delay of two cycles of the Z-phase signal compared with FIFO memory A 17. Therefore, FIFO memory C 19 stores video data (FIG. 3G), which is delayed by one video frames.

At the timing of letter a in FIG. 3G, for example, the order of data freshness is FIFO memory C, FIFO memory B, FIFO memory A with data in FIFO memory A oldest.

Figure 4:
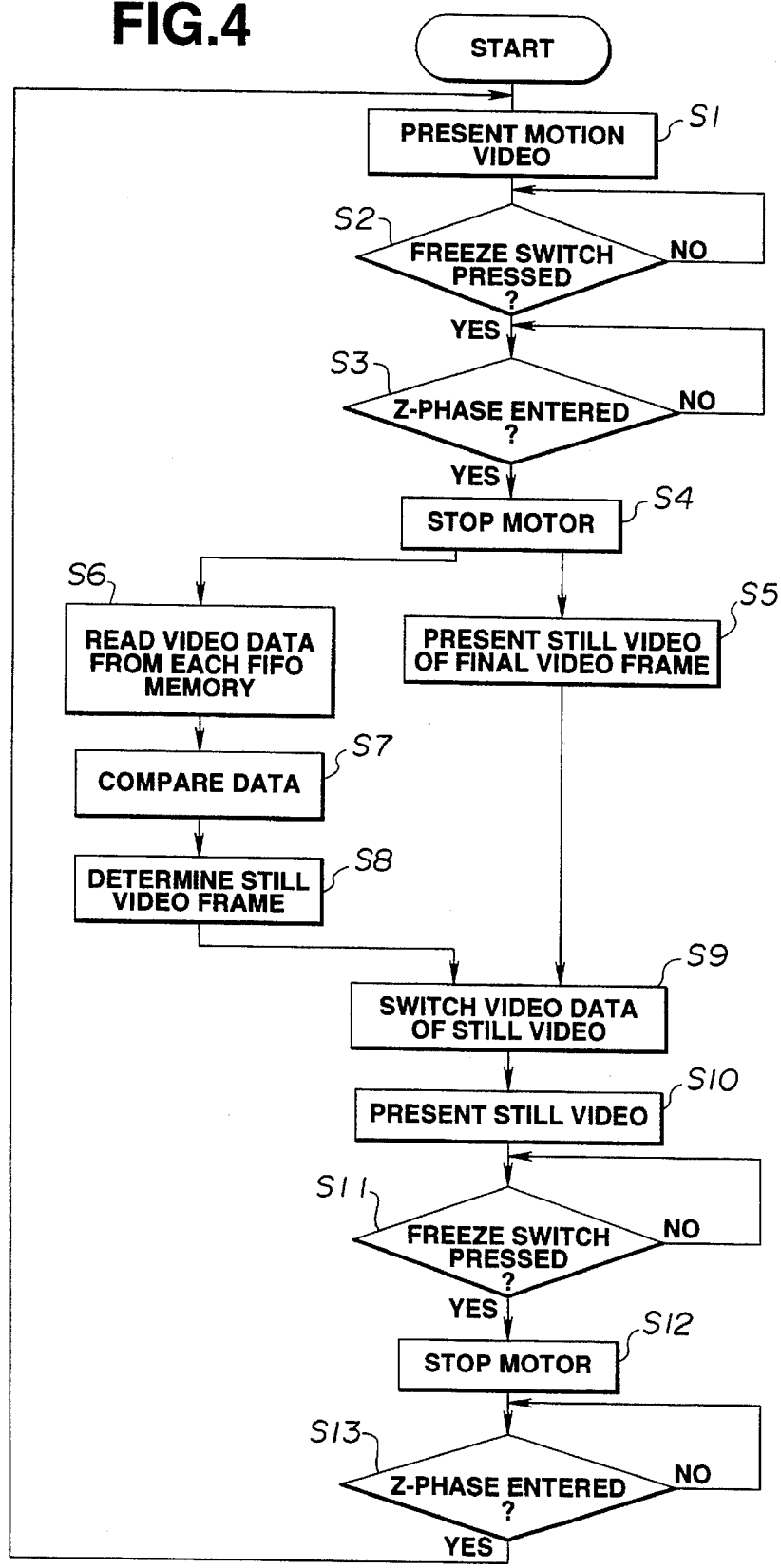

The process of detecting a video frame having the least distorted video data from among video frame data consecutive in time is now discussed referring to the flow diagram in FIG. 4.

With a motion video for a tomographic image presented at step S1, the freeze switch 10 on the ultrasonic endoscope 1 is pressed (S2). The Z-phase signal is entered (S3). At S4, the supply voltage to the motor 71 that rotates the mirror 72 is cut off and the motor 71 stops.

When the motor 71 stops, the data in FIFO memory A 17 as the final frame data is output at S5 and temporarily displayed. A still video is presented. At the same time, the reading of the video data stored in each of the FIFO memories 17, 18 and 19 starts at S6. The video data of the plurality of video frames read are compared to each other by the selector 20 according to a comparison sequence to be described later at S7. At step S8, the least distorted video frame among the video frames is determined to be presented as a still video.

When the video frame as a still video is selected, the selector 20 switches from the video data displayed at S5 to the least distorted video data determined at step S8 and outputs it at S9. At S10, the selected video is presented in still presentation. The least distorted still video is presented in this way.

When the freeze switch 10 is pressed again during still video presentation (S11), the motor 71 rotates again at S12. After the Z-phase signal is entered (S13), the process returns to S1, where still video presentation is shifted to motion video presentation. The above sequence is repeated each time the freeze switch is pressed.

The selection sequence to determine the least distorted video in steps S6 through S8 is now discussed.

Figure 2A:
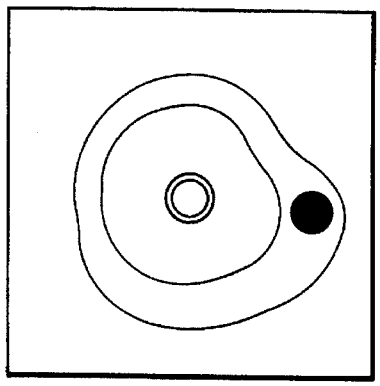
FIG. 2A shows an ultrasonic tomographic image without distortion.
Figure 2B:
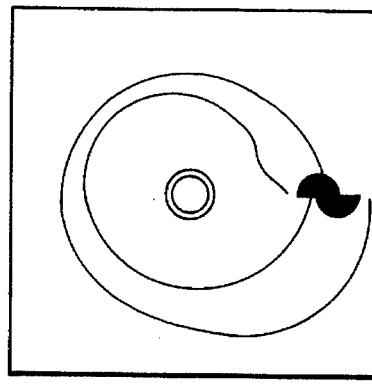
FIG. 2B shows an ultrasonic tomographic image distorted due to the movement of the body of a subject or transducer.
Figure 5:
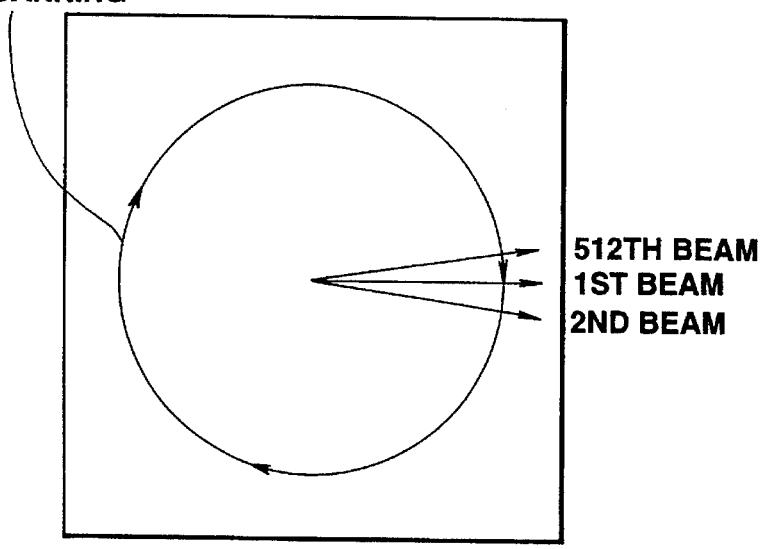

Video distortion in the tomographic image obtained through the mechanical scanning system (full-circle scanning system) is concentrated on the reference direction in scanning as shown in FIG. 2B (3 o'clock in this case). In this embodiment, it is assumed that 512 pulses or beams of ultrasonic wave are transmitted per full-circle scan. As shown in FIG. 5, of linear video data (sounding data or scanning data) obtained per pulse emission or beam in a sounding line, the degree of distortion in the reference direction in scanning is determined by comparing the video data on a first line or beam with the video data on a 512th line or beam. The selector 20 of the buffer memory block 16 compares both video data.

Figure 6:
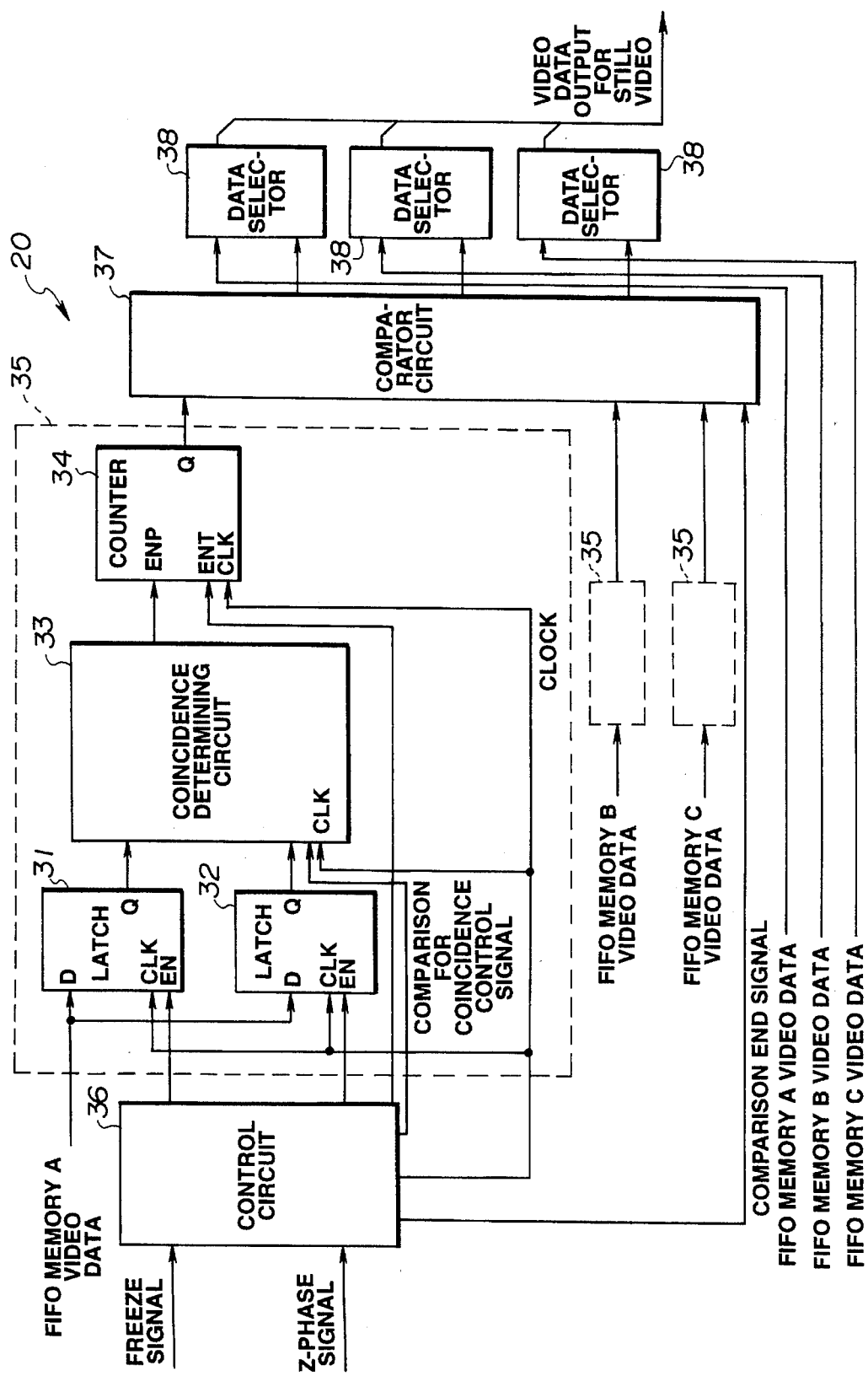

FIG. 6 shows the construction of the selector 20. The selector 20 comprises a coincidence block 35 made up of latches 31, 32, a coincidence determining circuit 33 and a counter 34, a control circuit 36, a comparator circuit 37, and a data selector 38. Each of FIFO memories A, B and C is provided with the respective coincidence block 35, with each memory connected to respective coincidence block 35.

FIG. 7A through 7L show the operation timing of each section of the selector 20. Referring to the timing diagram, the operation of the selector 20 is discussed. CPU 28 controls the selection sequence for the least distorted video data in the buffer memory block 16.

Figure 7:
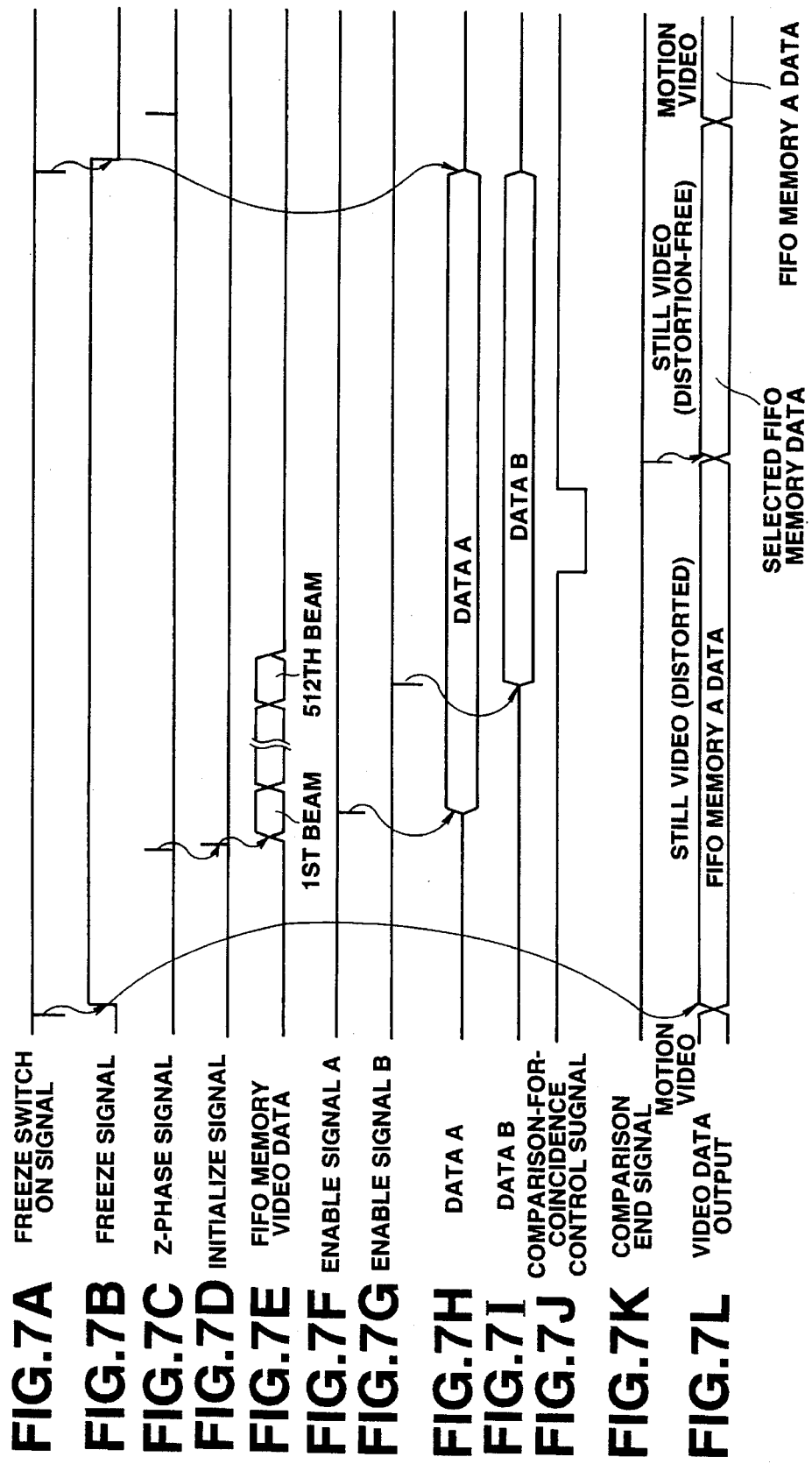

When the freeze ON or trigger signal (FIG. 7A) on the signal line 11 is driven low with the freeze switch 10 on the ultrasonic endoscope 1 pressed, CPU 28 outputs a high-level freeze signal (FIG. 7B) to the control circuit 36. When the Z-phase signal (FIG. 7C) comes in with the freeze signal at a high level, an initialize signal (FIG. 7D) that initializes the read address pointer of the FIFO memory is entered into the FIFO memory. As shown in FIG. 7D, the FIFO memory outputs sequentially the video data, from the one from the first beam to the one from the 512th beam.

The control circuit 36 sends an enable signal A (FIG. 7F) and an enable signal B (FIG. 7G) to latches 31, 32, respectively. The video data from each beam or line given by the FIFO memory is made up of 512 data, for example. Each of the first beam or line and 512th beam or line have 512 data. Data out of the 512 data in an arbitrary region (for example, 64 data of the 512 data) from each of the first line and the 512th line are stored in latches 31, 32, respectively in response to the enable signal A and enable signal B.

The data A and B (data length 64 data) stored respectively in latches A, B are sent to the coincidence determining circuit 33, where, for example, upper 4 bits of both data are compared for coincidence in response to a comparison-for-coincidence control signal (FIG. 7J) from the control circuit 36. When the coincidence determining circuit 33 determines a coincidence between the data A and data B, its output is sent to the counter 34 to cause it to count up. Coincidence determining is performed onto all 64 data, and the number of coincidences is counted by the counter 34.

The above process is simultaneously performed in each the three coincidence blocks 35 of FIFO memories A, B, and C in connection with three sets of video data. The count of the counter 34 in each of the coincidence blocks 35 is sent to the respective comparator circuit 37. When comparison for coincidence are fully performed to the video data in each of the FIFO memories, the control signal 36 sends a comparison end signal (FIG. 7K) to the comparator circuit 37.

The comparator circuit 37 compares the counts of the counters corresponding to the number of coincidences of the video data in FIFO memories in order to determine the video data having the largest count, namely determine a video frame having video data that has the best coincidence between the data in the first line and the data on the 512th line. The video information of the data selector 38 that is connected to the video data stored in the selected FIFO memory is determined as the video data in still video presentation, and then output. The selector 20 thus switches from the video data in FIFO memory A 17 (final video frame data) to the selected video data for still presentation and outputs it to the video memory 22. The apparatus thus presents a still video with less distortion at 3 o'clock.

When the freeze switch is pressed during motion video presentation as shown in FIG. 7B, the video data (FIG. 7L) as the output of the buffer memory block 16 is the video data in FIFO memory A 17, which is presented in still video as the final frame video data. Selected from among the video data in the plurality of FIFO memories is the least distorted video frame data that has the nearest approximation between the data at the scanning start line and the data at the scanning end line. The final frame video data is switched to the video data in the selected FIFO memory. Thus, the least distorted still video is presented.

In this embodiment, a distortion-free still video is obtained within about 10 ms after pressing the freeze switch (one video frame display time is 33 ms).

As described above, according to the embodiment 1 of the present invention, a distortion-free still video is obtained in tomographic images in ultrasonic endoscopic diagnosis. In the prior art, freeze operation must be repeated until a proper still video with no distortion is obtained. In this embodiment, a single freeze operation offers a distortion-free still video. Diagnosing time, which could otherwise be prolonged by repeated freeze operations, is shortened.

A freeze operation is a single operation without extra operation for still video correction. Since the operator is thus allowed to practically continuously hold the endoscope, the ease of use is substantially improved. If the operator is forced to let his hands off the endoscope, the operator's attention may be drawn from the region-of interest of the subject. Such an inconvenience is avoided and an increase of diagnosing time is prevented.

In this embodiment, when video distortion affects a plurality of video frames prior to a stop of scanning, the least distorted video data is selected and thus more severely distorted video data that is attributed to the movement of the body or transducer is rejected.

This embodiment employs the scanning means in which the mirror 72 looking to the ultrasonic transducer 4 is rotated to scans ultrasonic wave. Alternatively, to rotate it, the ultrasonic transducer 4 may be mechanically linked to the axis of rotation of the motor 71, directly or via intermediate shafts. Rotation, linear motion, spiral motion or pivotal motion of the radiating face of the transducer may be used.

Figure 8:
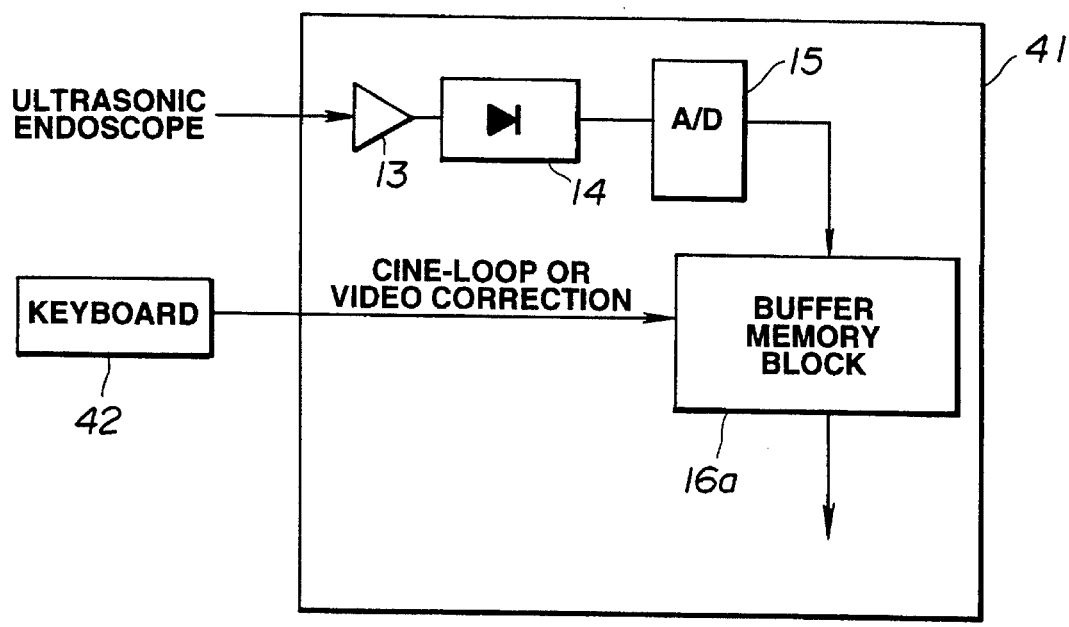
FIGS. 8 and 9 are related to embodiment 2 of the present invention.
Figure 9:
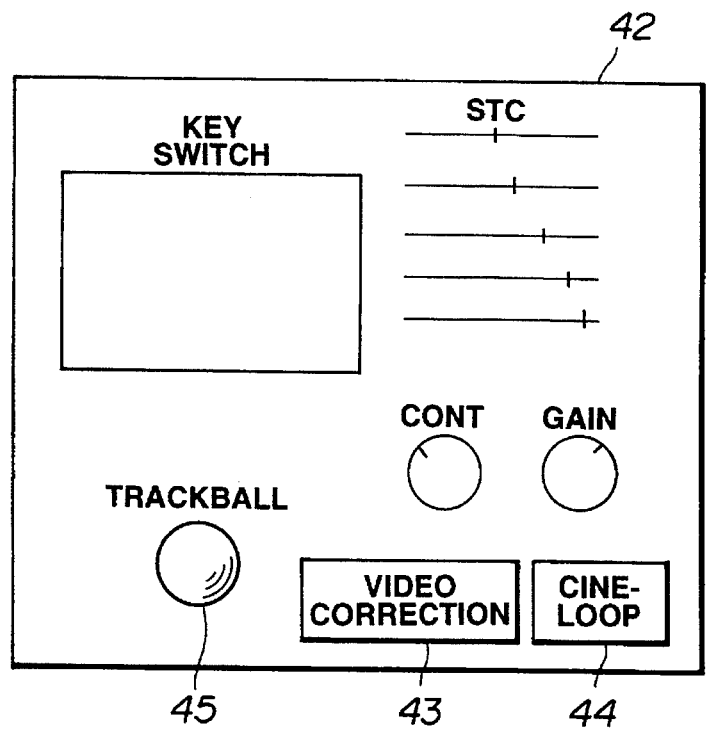

Referring to FIGS. 8 and 9, the embodiment 2 of the present invention is now discussed. The embodiment 2 is provided with video correction function and cine-loop function in the ultrasonic control unit.

The ultrasonic control unit 41 in the embodiment 2 has a buffer memory block 16a having a larger memory capacity. In addition to the construction in the embodiment 1, the embodiment 2 is provided with the cine-loop function that allows the buffer memory block 16a to output video data to be displayed in cine-loop presentation in such a way that video varies sequentially in time like motion-picture film, though no detail diagram is provided herein. The rest of the construction remains unchanged from the embodiment 1.

The ultrasonic control unit 41 connects to a keyboard 42. In response to the operation of the keyboard 42, the ultrasonic control unit 41 gives to the buffer memory block 16a a function switching signal that switches between the video correction function and the cine-loop function.

FIG. 9 shows the panel layout of the keyboard 42. Disposed on the keyboard 42 are a video correction switch 43 for selecting the video correction function, a cine-loop switch 44 for selecting the cine-loop function, and a trackball 45 for manipulating the image during cine-loop presentation.

Ultrasonic wave scans the target region in the subject body. Ultrasonic diagnosis is performed based on the tomographic image which the ultrasonic control unit 41 produces from the ultrasonic echo signal. With the cine-loop switch 44 selected on the keyboard 42, the trackball 45 is allowed to select the outputs of FIFO memories A, B, and C in the buffer memory block 16a. The content of the video data stored are FIFO memory C, FIFO memory B and FIFO memory A in the order of freshness with the FIFO memory A oldest. When the trackball 45 is manipulated, the video data stored in each FIFO memory is output and the monitor gives images in the cine-loop presentation, like a motion-picture film in which the image changes sequentially in time.

With the video correction switch 43 turned on the keyboard 42, the buffer memory block 16a determines the degree of coincidence at 3 o'clock in the video data in each of the FIFO memories A, B, and C in the same way as in the embodiment 1. The least distorted video frame data is selected as the output to the monitor, where its still video is presented.

In this embodiment, the FIFO memories in the buffer memory block 16a are used for both the cine-loop presentation and distortion-free still video presentation. Therefore, in addition to the advantage of the embodiment 1, the cine-loop presentation is available as necessary after the freeze operation. The operator can immediately switch back to distortion-free still video to record it. The operation can thus enjoy both functions at will.

Figure 10:
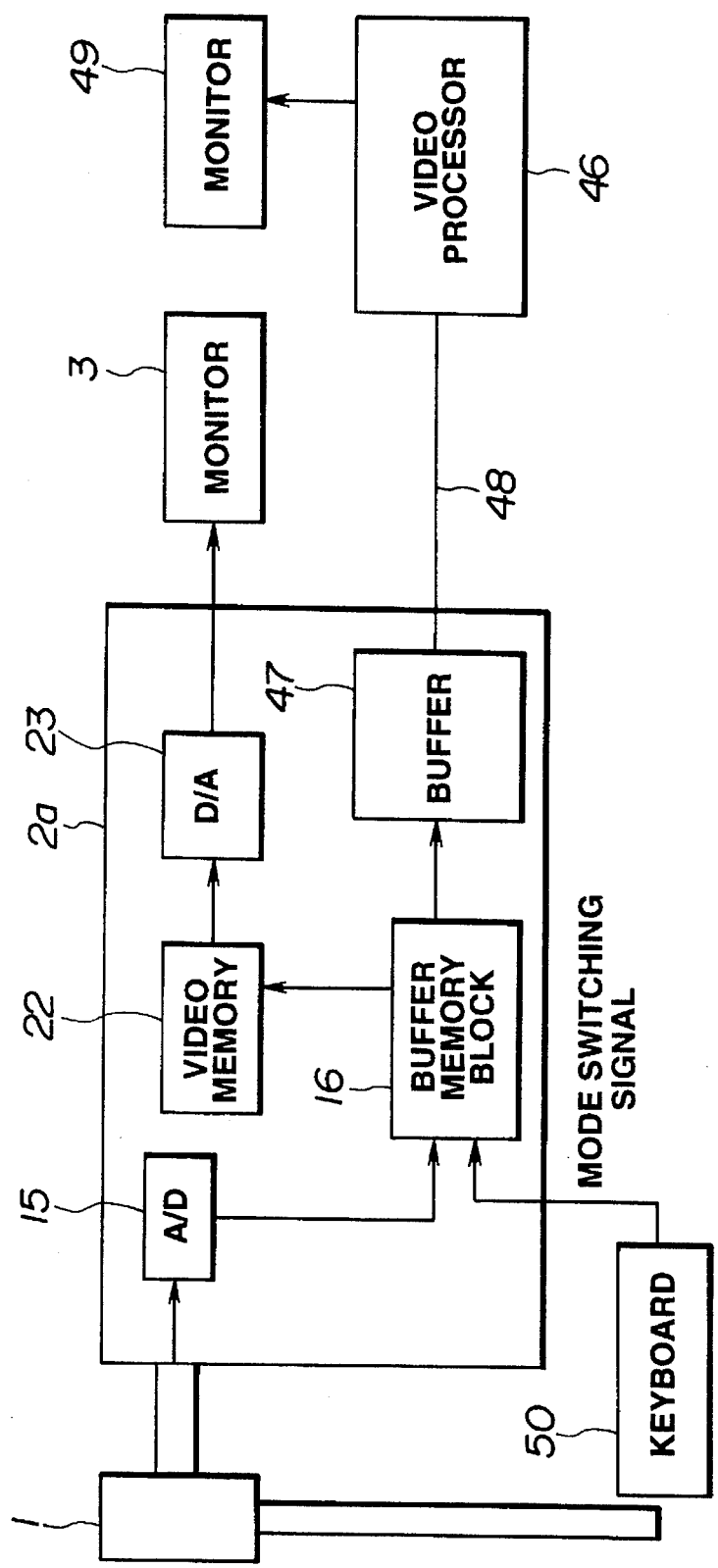
FIG. 10 is a block diagram showing generally the construction of the ultrasonic diagnosing apparatus according to embodiment 3 of the present invention.

FIG. 10 is the block diagram showing generally the ultrasonic diagnosing apparatus according to the embodiment 3 of the present invention. In addition to the ultrasonic endoscope 1 and the ultrasonic control unit 2a, the embodiment 3 comprises a video processor unit 46 that performs more sophisticated video processing (for example, image correction such as post-processing, three-dimensional presentation, and tissue texture diagnosing).

As in the embodiment 1, the ultrasonic control unit 2a comprises the A/D converter 15, the buffer memory block 16, the video memory 22, and the D/A converter 23. Furthermore, the ultrasonic control unit 2a comprises a buffer 47 for transferring data to an external video processor unit 46. The buffer 47 is connected to the video processor unit 46 via a transmission cable 48. Data exchange is performed between the ultrasonic control unit 2a and the video processor unit 46 via the buffer 47 and the transmission cable 48.

Separately from the monitor 3 connected to the ultrasonic control unit 2a for ultrasonic image presentation, another monitor 49 is provided to present a processed image. The monitor 49 is connected to the video processor unit 46. The ultrasonic control unit 2a connects to a keyboard 50, through which a command such as the one for entering a mode switching signal is input.

With the keyboard 50 operated, the mode switching signal is input to the buffer memory block 16 in the ultrasonic control unit 2a to selectively switch between the still video mode for presenting the least distorted video and a video processing mode for transferring the video data that is suited for video processing by the video processor unit 46.

When the keyboard 50 selects the still video mode, the buffer memory block 16 sends the video data stored in each of the FIFO memories to the selector to select the least distorted video frame data and outputs the selected video data to the video memory 22, in the same way as in the embodiment 1. This video data output is sent via the video memory 22 and the D/A converter 23 to the monitor 3, where the least distorted video is presented in still mode.

When the keyboard 50 selects the video processing mode, the buffer memory block 16 arranges the video data stored in the FIFO memories into a format that is compatible with the video processor unit 46, and outputs it to the buffer 47. The video data output is sent from the buffer 47 to the video processor unit 46 via the transmission cable 48. The video processor unit 46 performs a desired video processing such as image correction and the resulting processed video is presented on the monitor 49.

This embodiment allows the buffer memory block to switchably work to transfer data to an external device such as the video processor unit or to select the least distorted video data for still video presentation. In addition to the advantage offered by the embodiment 1, this embodiment meets either of the operator's requirements: performing sophisticated video processing during diagnosis and obtaining quickly a distortion-free still video for recording after a freeze operation.

Figure 11:
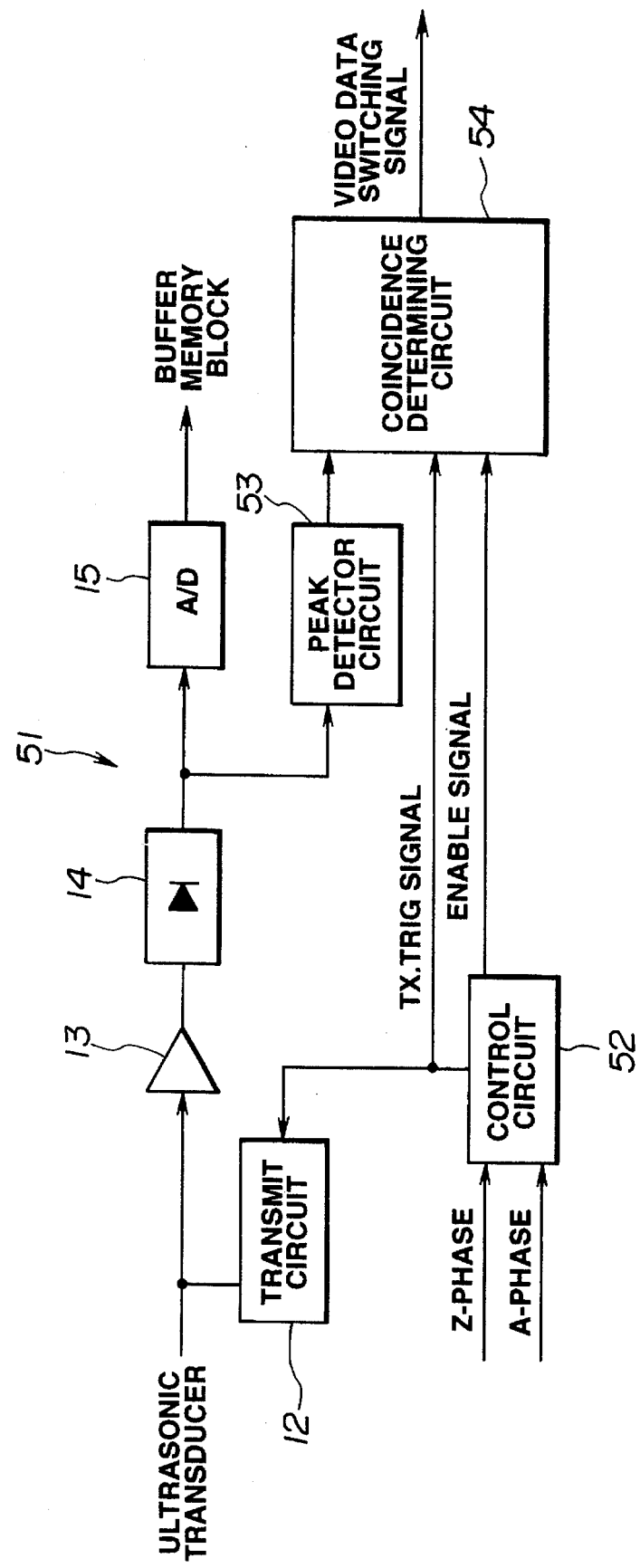
Figure 12:
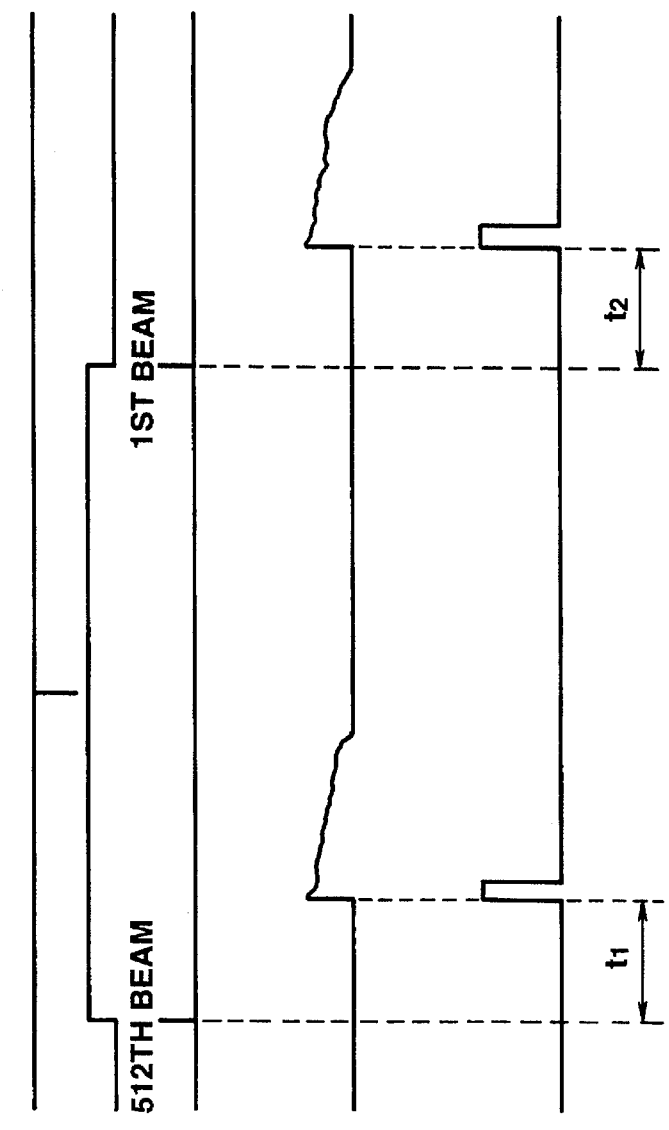

The embodiment 4 of the present invention is now discussed referring to FIGS. 11 and 12.

The ultrasonic control unit 51 in the embodiment 4 comprises a control circuit 52 for outputting synchronizing signals and control signals, such as a TX TRIG signal, in response to the A-phase and Z-phase signals, a peak detector circuit 53 for detecting a peak of the output of the detector circuit 14, and a coincidence determining circuit 54 for selecting the least distorted video based on the peak position of the echo signal detected by the peak detector circuit 53. The rest of the construction of the embodiment 4 remains unchanged from that of the embodiment 1.

Discussed next is the selection operation of the ultrasonic control unit of the embodiment 4 for the least distorted video, referring to FIG. 12A through 12E.

The control circuit 52 outputs TX TRIG signals (FIG. 12C) on the first line and 512th line in response to the Z-phase signal (FIG. 12A). The control circuit 52 also outputs an enable signal (FIG. 12B) indicative of the interval between the first line and the 512th line.

The peak detector circuit 53 detects a peak of the demodulated signal (FIG. 12D) of the echo signal output by the detector circuit 14. The peak position corresponding to the peak of the demodulated signal represents, for example, the boundary between water and the tissue of the subject body. The peak signal (FIG. 12E) detected by the peak detector circuit 53 therefore represents the echo reflected from the boundary. When echoes result from a gap or other objects surrounding the ultrasonic transducer, erroneous peak detection is prevented by making the peak detector circuit 53 not recognizing any peak for an arbitrary duration of time in succession to the moment of the TX TRIG signal output.

The coincidence determining circuit 54 receives the peak signal, the enable signal and the TX TRIG signal. The coincidence determining circuit 54 counts t1, t2, between the timing of the TX TRIG signal during the high-level of the enable signal (the interval between the first line and the 512th line) and the timing of the peak signal.

The counting of t1, t2 is performed each time the FIFO memories in the buffer memory block 16 receive video data. The coincidence determining circuit 54 stores t1, t2 for the video data in each video frame, determines each video frame for coincidence between t1 and t2, and selects the video data having the nearest time approximation between t1 and t2 as the least distorted video frame data for still video presentation.

A video data switching signal is sent to the selector of the buffer memory 16 to select one from among the FIFO memories. The video data in the selected FIFO memory is output to the video memory 22 to be displayed as a still video with the least distortion at 3 o'clock direction.

When t1 and t2 are close in their values, the tomographic image shows a continuity between the first line and the 512th line. When there is a large difference between t1 and t2, the image suffers a discontinuity between the first line and the 512th line. In this embodiment, by displaying the video frame having the closet time count between t1 and t2, the image with little distortion between the first and 512th lines is selected for presentation.

Furthermore, since video distortion detection is processed in analog form, this embodiment selects the least distorted image with the shortest process time in addition to the advantage of the embodiment 1. The embodiment 2 is advantageous when the operator wants to achieve a high-speed scanning and expedite the process from distortion detection to video switching for still video presentation. A short diagnosing time thus results.

Figure 13:
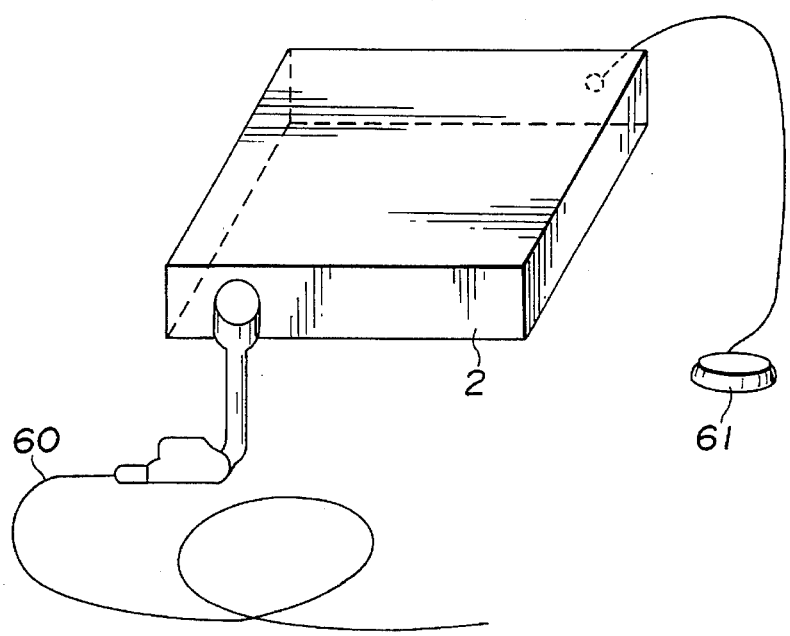
FIG. 13 is an explanatory view showing the construction of the ultrasonic diagnosing apparatus according to embodiment 5 of the present invention.

FIG. 13 shows the construction of the ultrasonic diagnosing apparatus according to the embodiment 5 of the present invention.

The embodiment 5 employs a small-diameter ultrasonic probe 60 as an ultrasonic scanner for transmitting and receiving ultrasonic wave, instead of the ultrasonic endoscope. The ultrasonic control unit 2 connects to the ultrasonic probe 60. The ultrasonic probe 60 has on its end a probe insert portion having an unshown ultrasonic transducer. The probe insert portion is inserted into the body of the subject to scan ultrasonic wave and to acquire an ultrasonic tomographic image. The ultrasonic control unit 2 is provided with a foot-pad switch 61 that allows the operator to control the ultrasonic transducer on the ultrasonic probe 60 for starting or stopping scanning.

In the embodiment 1, when the freeze switch on the ultrasonic endoscope is pressed, a still video is presented while the selection of the least distorted video is automatically performed as detained in the flow diagram in FIG. 4. On the other hand, the embodiment 5 uses the foot-pad switch 61, instead of the freeze switch, to start or stop scanning of the transducer on the ultrasonic probe 60. The presentation of the still video and the selection of the least distorted video are performed in the same way as in the embodiment 1.

The embodiment 5 thus arranged offers the same advantage as the embodiment 1.

Figure 14:
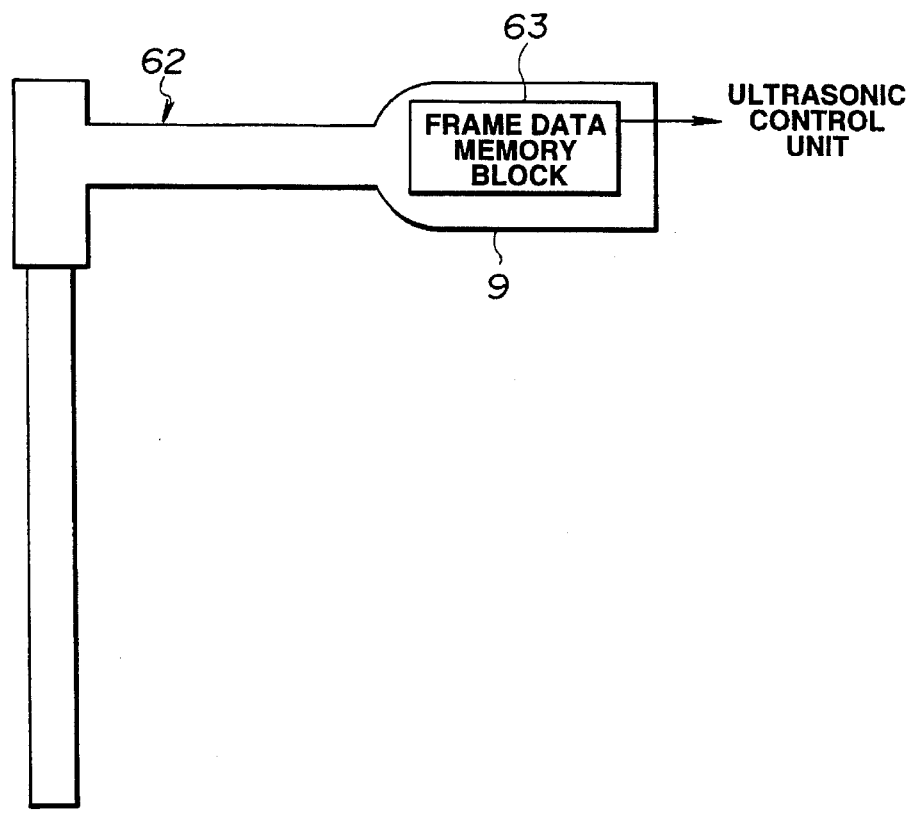
FIG. 14 is a block diagram showing the ultrasonic endoscope contained in the ultrasonic diagnosing apparatus according to embodiment 6 of the present invention.

FIG. 14 is the block diagram showing the construction of the ultrasonic endoscope in the ultrasonic diagnosing apparatus according to the embodiment 6 of the present invention.

The ultrasonic diagnosing apparatus of the embodiment 6 comprises, in the ultrasonic connector 9 in each ultrasonic endoscope 62, a frame data memory block 63 that checks each probe regarding which frame, prior to a freeze operation, offers the least distorted video, and stores such empirical data. Based on the data in the frame data memory block 63, the least distorted video frame data is selected for presentation.

The ultrasonic scanner with the ultrasonic transducer is not limited to the already described ultrasonic endoscope. The ultrasonic probe in FIG. 13 may be acceptable. Each scanner is provided with the respective frame data memory block.

When the ultrasonic endoscope 62 connects to the ultrasonic control unit, the frame data empirically acquired and stored in the frame data memory block 63 is transferred to the control circuit or the like in the ultrasonic control unit. When the operation of the freeze switch allows the still video to be presented, which frame, prior to the freeze operation, offers the least distorted video data is determined based on the frame data. The selected least distorted video data is output through the buffer memory block to be displayed.

As described above, the embodiment 6 stores and uses later the frame data, which is obtained prior to the freeze operation, and which offers the least distorted video. The embodiment 6 selects and presents the least distorted video data as the embodiment 1 does. Furthermore, the embodiment 6 needs no particular video selection process for selecting the least distorted video, and thus permits an instant switchover to the stored video.

Alternatively to the embodiment 6, the ultrasonic control unit may be contains the frame data memory block. In this case, the connector of the ultrasonic endoscope may be provided with type identification means such as code indicative of the type of the ultrasonic endoscope. Referring to the type identification means, a connected endoscope is determined and the corresponding frame data is read. Based on the read frame data, the least distorted video data is selected and output from the buffer memory block for presentation.

The alternative embodiment thus arranged offers the same advantage as the embodiment 6.

The above embodiments have been described with reference to the mechanical scanning ultrasonic endoscope. The above embodiments also work on an electronic full-circle scanning endoscope to be described later. Namely, video quality improvement effect is achieved if the above-described video distortion detection means is applied to the image the electronic full-circle scanning endoscope presents.

Referring to FIGS. 15 through 18C, the electronic full-circle scanning endoscope is discussed.

Figure 15:
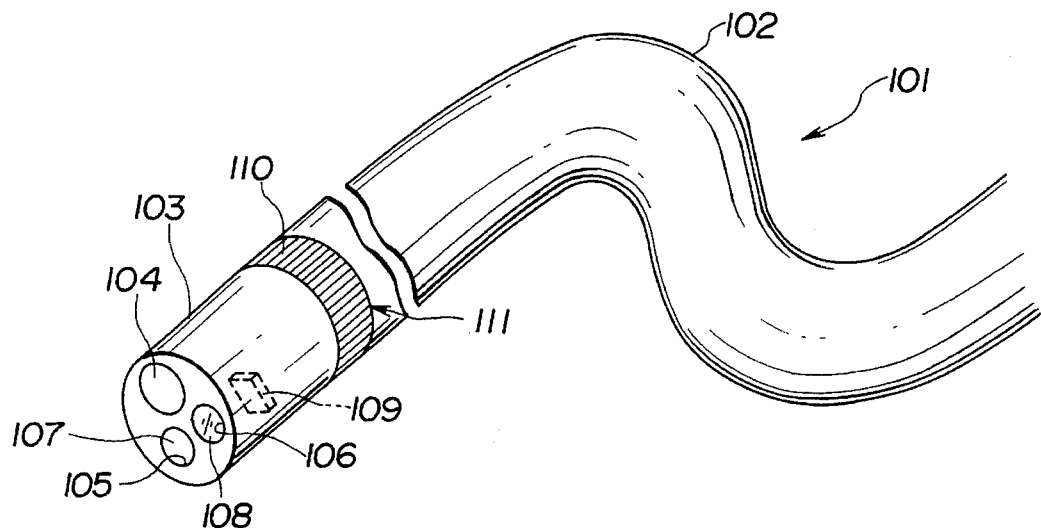

As shown in FIG. 15, the electronic full-circle scanning ultrasonic endoscope 101 comprises a flexible long insert assembly 102, and, at the end portion 103 of the insert assembly 102, the port of the clamp channel 104, an illumination window 105 for projecting light, and a viewing window 106 for optical viewing.

The distal end of a light guide 107 is attached to the illumination window 105. The light guide 107 conducts illumination light from an unshown proximal end to the distal end, from which light is projected. An objective lens 108 is mounted onto the viewing window 106 to form an optical image. CCD 109 as a solid-state image pickup device is mounted at the point of focus of the objective lens 108 in order to photoelectrically converts the optical image.

A ring of ultrasonic transducers 110 are arranged in a narrow pitch around the end portion 103 of the insert assembly 102. The ring of ultrasonic transducers 110 constitute a transducer array 111.

Figure 16:
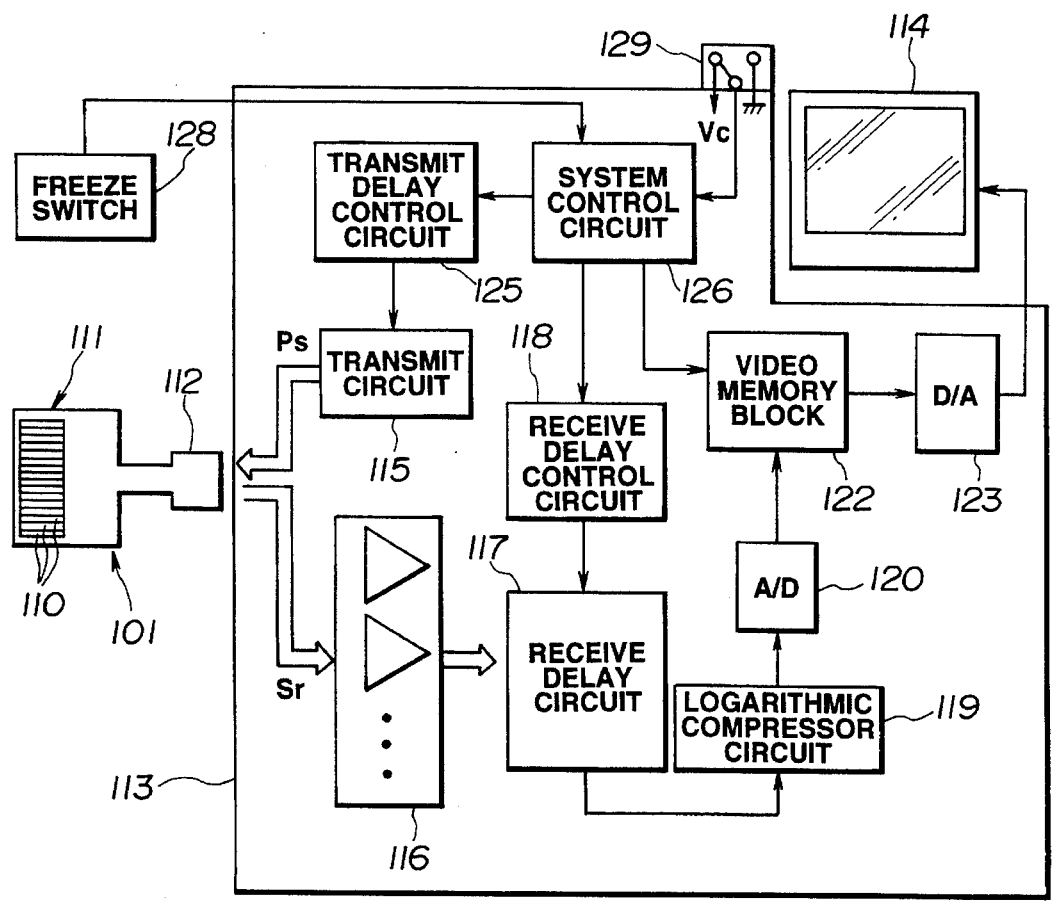

As shown in FIG. 16, the connector 112 of the electronic full-circle scanning ultrasonic endoscope 101 is connected to the connector socket of the ultrasonic control unit 113. The echo signal received by the transducer array 111 is sent to signal processor means in the ultrasonic control unit 113, and the resulting ultrasonic diagnosing image is presented on a monitor 114.

Referring to FIG. 16, the internal construction of the ultrasonic control unit 113 is discussed. The ultrasonic control unit 113 comprises a transmit circuit 115 for feeding a high-tension pulse signal Ps to the plurality of transducers 110 in the electronic full-circle scanning ultrasonic endoscope 101 (for the transducers 110 to transmit ultrasonic wave), and a plurality of preamplifiers 116 for amplifying the received signal given by each of the transducers 110. Both the transmit circuit 115 and the preamplifiers 116 are connected to each of the transducers 110 via the connector socket that is mated with the connector 112 of the endoscope 101.

The output of each preamplifier 116 is sent to a receive delay circuit 117 that delays its input signal. The receive delay circuit 117 connects to a receive delay control circuit 118 that controls the length of delay.

The output of the receive delay circuit 117 is sent to a logarithmic compressor circuit 119 that performs logarithmic compression. The output of the logarithmic compressor circuit 119 is sent to an A/D converter 120 that performs analog-to-digital conversion. The output of the A/D converter 120 is sent to a video memory block 122 that contains a mass video memory 121. The mass video memory 121 has a mass memory sufficient to store a large amount of video data equal to a great deal of video frames.

The output of the memory block 122 is sent to a D/A converter 123 that performs digital-to-analog conversion. The output of the D/A converter 123 is fed to a monitor 114.

The transmit circuit 115 connects to a transmit delay control circuit 125, which controls the delay length of the high-tension pulse signal Ps provided by the transmit circuit 115. A system control circuit 126 controls delay control circuits 118, 125 and the video memory block 122.

Figure 17:
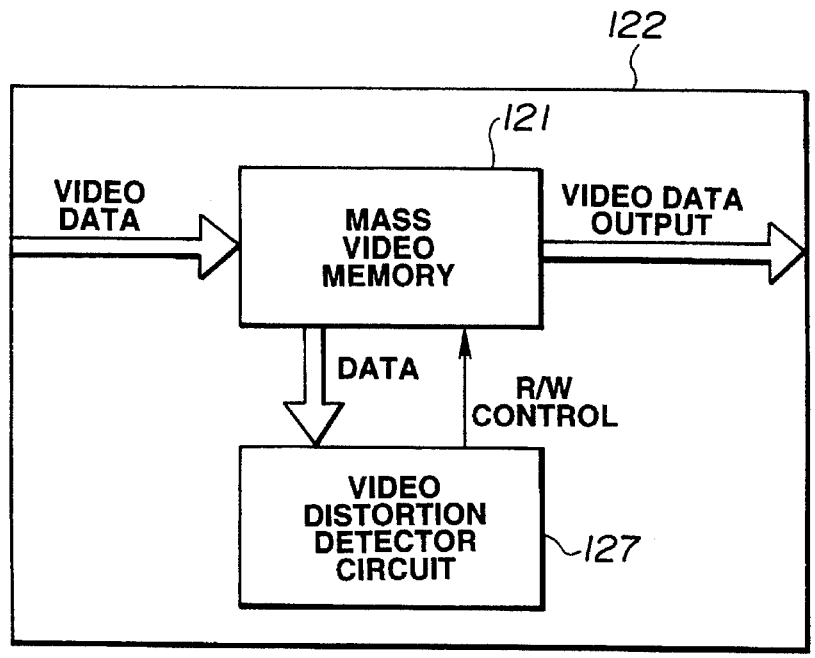

As shown in FIG. 17, the video memory block 122 is provided with a video distortion detector circuit 127 that is equivalent to the one equipped in the already-described mechanical scanning system. The video distortion detector circuit 127 receives a plurality of frames of video data, selects the least distorted video, and allows it to be output from the mass video memory 121.

A freeze switch 128 mounted external to the ultrasonic control unit 113 connects to the system control circuit 126. When the freeze switch 128 is operated, the system control circuit 126 activates the video distortion detector circuit 127 so that it selects and displays the least distorted video freezed.

Figure 18A:
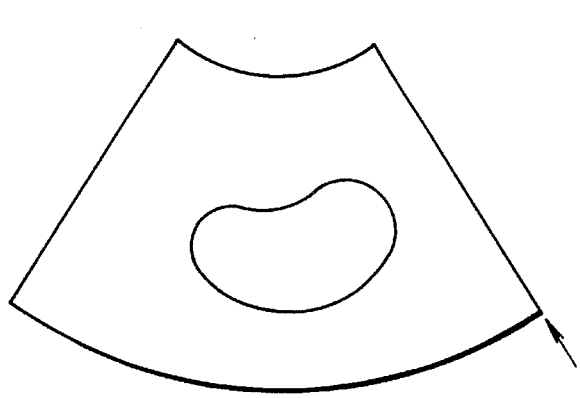
Figure 18B:
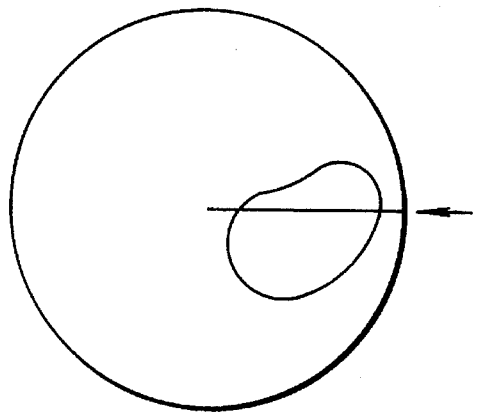

A scanning range selector switch 129 is provided to set the scanning range to a predetermined sector angle. This switch 129 give to the operator two options: sector scanning operation as shown in FIG. 18A and full-circle scanning operation as shown in FIG. 18B. The arrow in FIG. 18A represents the direction of the scanning start. In FIG. 18B, the arrow shows a sounding line.

The operation of the ultrasonic control unit 113 is now discussed. Suppose that the scanning range selector switch 129 selects the full-circle scanning operation. In the same way as in the mechanical scanning system, when the freeze switch 128 is operated, the video distortion detector circuit 127 calculates the degree of distortion or discontinuity at 3 o'clock direction for each of the plurality of video frames of video data stored in the video memory block 122. The video frame of the least degree of discontinuity is selected and output to the D/A converter 123 and then displayed on the monitor 114.

When the freeze switch 128 is operated with the sector scanning operation selected, the video distortion detector circuit 127 in the video memory block 122 compares two adjacent line data at the start of the scanning, selects the video frame of video data that has the highest degree of coincidence, and sends the video data of the selected video frame to the monitor 114 via the D/A converter 123.

This embodiment offer the following advantages.

Since the ultrasonic endoscopic diagnosing by entering the endoscope into the body cavity of the subject must view lesions smaller than a few millimeters, sometimes, lesions smaller than a millimeter, high bearing and range resolutions are required compared with extracorporeal ultrasonic diagnosing.

To achieve a high bearing resolution, the ultrasonic control unit is designed to output 1000 beams or sounding lines per full-circle scanning (An ordinary extracorporeal ultrasonic control unit typically offers 100 to 200 beams or sounding lines).

To reduce the sidelobes of the beams as much as possible, the number of transducers 110 may be increased. To improve the overall resolution of the display screen, the number of stages of a known multi-electronic focusing may be increased.

Even if the electronic scanning is used to improve the resolutions, the frame rate of the video is reduced to 10 frames/second or so. Therefore, when the electronic scanning is used in the body cavity, a low frame rate is used.

When the full-circle scanning ultrasonic endoscope is used, its display is PPI. In this case, if a low frame rate is used, a resulting image suffers a discontinuity at the start line (at 3 o'clock, for example).

A poor continuity of an image due to a low frame rate in the full-circle scanning system is more pronounced than in a linear or sector scanning system. Since the discontinuity line in the linear or sector scanning system comes to the edge of the display area, the discontinuity line rarely interferes with the region of interest (ROI). In the full-circle scanning, however, the discontinuity line extends from center along the 3 o'clock direction, it frequently interferes with ROI (Refer to FIGS. 18A and 18B).

This embodiment offers an improved image quality in the image after the freeze operation even in the electronic scanning system.

FIG. 19 shows the embodiment 8 of the present invention, wherein the ultrasonic control unit comprises a color Doppler circuit. The use of video distortion detection function in the unit achieves an improved quality image after freeze operation.

The transmission pulse from a transmit circuit 132 in the ultrasonic control unit 131 is supplied to an unshown transducer. In the transmit circuit 132, an oscillator 0s oscillates at a reference frequency and outputs an oscillation signal. The transmit circuit 132 converts the oscillation signal into a pulse signal, which is then applied to a pulse generator circuit 134. The pulse generator circuit 134 generates the transmission pulse.

The ultrasonic echo signal received by the transducer is converted into an electrical signal, which is then fed to a receiver circuit 135. The output of the receiver circuit 135 is detected by a detector circuit 136, and then fed via an A/D converter 137 to a video memory block 138 for B-display mode. The video memory block 138 contains a mass memory 139 and a video distortion detector circuit 140.

The output of the mass memory 139 is sent to an encoder 142 via a D/A converter 141 as a luminance signal Y. The encoder 142 converts the luminance signal Y and a color signal to be described later into a color video signal, which is then fed to a color monitor 143.

The output of the receiver circuit 135 is sent to a color Doppler circuit 144. The signal input to the color Doppler circuit 144 is multiplied by the oscillation signal from the transmit circuit 132 by a multiplier 145. The multiplied signal is subjected to an LPF 146, which passes a difference signal component only. Thus, a Doppler signal component is extracted.

Accordingly, a shifted frequency component of the echo signal relative to the transmitted ultrasonic frequency is thus extracted. This frequency component is detected by a detector circuit 147, sent to an A/D converter 148 and then sent to a color Doppler display mass memory 149 to be written there.

The color Doppler display mass memory 149 and B-display mode mass memory 139 connect to the video distortion detector circuit 140. For example, when the freeze switch is operated, the video distortion detector circuit 140 performs video distortion detection operation to the video in the mass memory 139. The video of the least distorted video frame is output from the mass memory 139 while the Doppler video corresponding to the least distorted video frame is output from the mass memory 149.

The Doppler video output from the mass memory 149 is corrected by a corrector circuit 150. When data representing the angle between the running direction of blood vessel and the direction of ultrasonic projection is entered using an unshown keyboard, the corrector circuit 150 corrects the Doppler component to the value representing the correct speed of bloodstream based on the data.

The output of the corrector circuit 150 is fed to the encoder 142 via a D/A converter 133 as the color signal C. The encoder 142 composites moving parts such as blood stream into a quasi-color image signal, and its amplitude varies according to the speed of bloodstream. The color monitor 143 presents color Doppler video in which blood vessel parts change their chroma according to bloodstream speed.

When a freeze operation is activated, the distortion at 3 o'clock in the B-display mode is calculated. Among the video frames prior to the freeze operation, the video frame that has suffered the least distortion in the B-display mode is detected. At the same time, the video distortion detector circuit 140 controls the color Doppler display mass memory 149 so that the color Doppler video having the same timing correspondence with the selected B-display mode video is output.

As a result, the freeze operation shifts the monitor from motion video to still video presentation. The intensity-modulated image in the B-display mode and the color Doppler video are superimposed into a false-color image, which suffers the least distortion.

In the motion-video presentation, the color Doppler circuit 144 presents no Doppler video.

This embodiment offers the following advantages.

When the color Doppler ultrasonic control unit is applied for laparoscopic diagnosis, color presentation of bloodstream at a speed as slow as a few millimeters/second to a few centimeters/second is required (in the circulatory system, a high-speed bloodstream on the order of a few meters/second is measured).

When such slow bloodstream is color presented, the time constant of the known MTI filter provided to reduce color presentation attributed to the motion of an organ is set to be large. As a result, the frame rate of the video is reduced to a small value as small as a few frames/second.

To diagnose on the video presentation at such a slow frame rate, a patient may be requested to hold his breath for a moment, and ROI is color presented in motion-video mode. However, if the video is distorted when the motion-video mode is switched to still video presentation for recording, another diagnosing may be required.

This embodiment helps prevent or reduce such a video distortion. Thus, diagnosing time may be shortened in laparoscopic color Doppler diagnosing.

Figure 20:
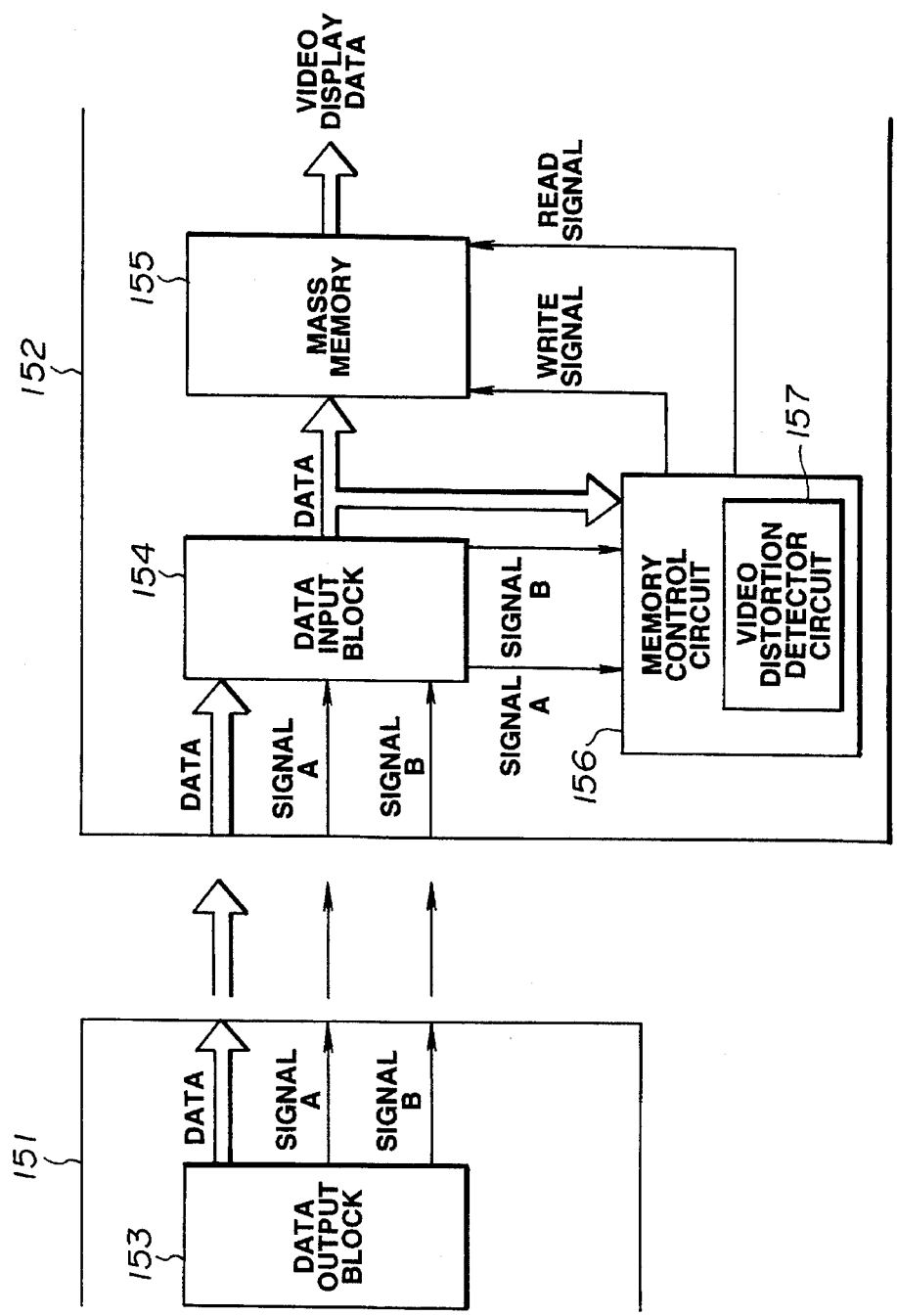
FIGS. 20 through 22 are related to embodiment 9 of the present invention.

FIG. 20 shows the major portion of the embodiment 9 of the present invention. The embodiment 9 comprises a video distortion detector circuit in the sophisticated video processor unit (for performing image correction such as post-processing) described with reference to the embodiment 3.

An ultrasonic control unit 151 has a data output block 153 for transferring received data to an external video processor unit 152. The video processor unit 152 has a data input block 154 for receiving the data transmitted from the ultrasonic control unit 151.

The output of the input data block 154 is input to a mass memory 155 that is capable of storing video data of tens of video frames. The mass memory 155 connects to a memory control circuit 156 that controls read/write operation to the mass memory 155. The memory control circuit 156 contains the video distortion detector circuit 157 that reads data from the mass memory 155 and detects the degree of distortion of each video frame.

Referring to FIGS. 21A through 21C and 22, the operation of this embodiment is discussed from the standpoint of the data exchange between the ultrasonic control unit 151 and the video processor unit 152.

Figure 22:
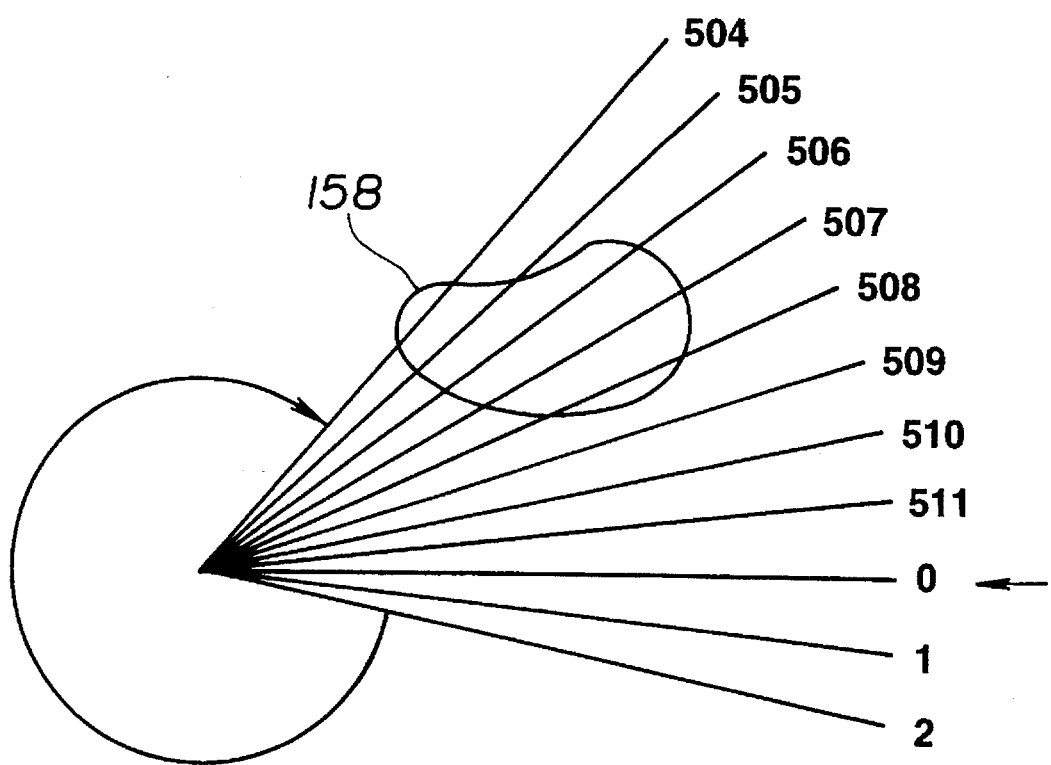

As shown in FIG. 22, a single full-circle scan offers data of 512 sounding lines, for example. Suppose that the sounding line that starts drawing a video is at 3 o'clock position as shown in FIG. 22. FIG. 22 shows that ultrasonic wave scans the lesion 158.

Figure 21:
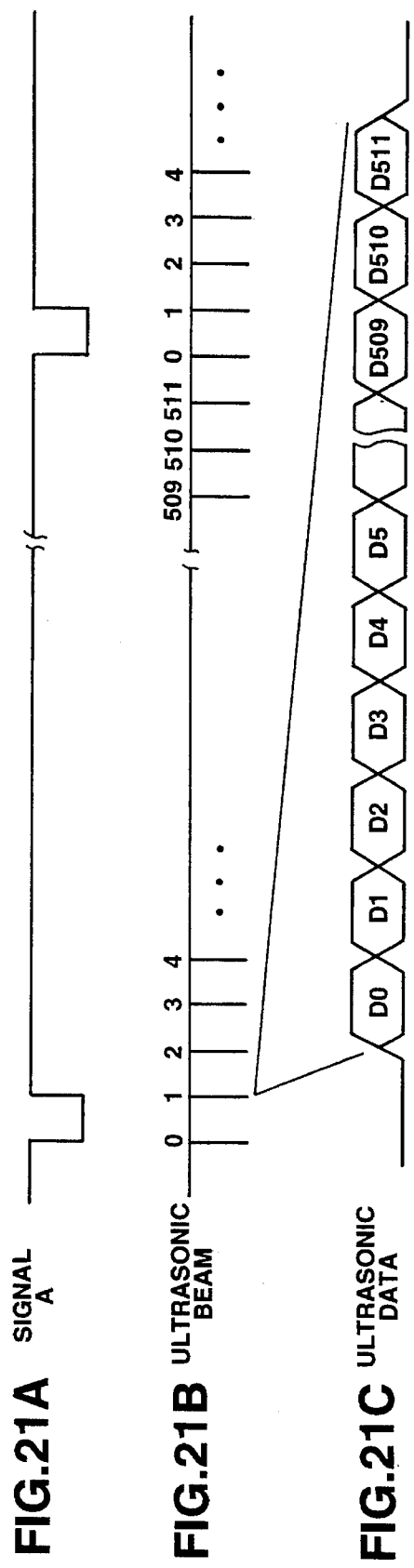

The sounding lines are numbered sequentially clockwise, 0 1, 2, ..., 511 with the sounding line at 3 o'clock starting with "0". The sounding line numbers again start over with 0 in a clockwise direction. Each sounding line results in 512 received data (D0, ..., DS11) as shown in FIG. 21C.

These received data are transferred from the control unit 151 to the external video processor unit 152. In this case, the signal A representing the start timing of video drawing by the first sounding line and the signal B representing the output timing of each sounding line data are together sent to the external video processor unit 152.

In the video processor unit 152, the memory control circuit 156 writes the video data coming from the control unit 152 onto the mass memory 155 according the timings of the signals A and B. In the motion-video mode, the video data written onto the mass memory 155 is sequentially read, transferred to the later stages as the video display data and then displayed on the monitor.

The data for sounding line numbers "511" and "0" that is written onto the mass memory 155 is sent from the data input block 154 to the memory control circuit 156, where the video distortion detector circuit 157 detects the degree of distortion of each video frame.

When a freeze operation is made, the memory control circuit 156 selects and reads the least distorted video frame from among the plurality of video frames stored in the mass memory 155, and then outputs the still video data with the least degree of discontinuity at 3 o'clock to the later stages so that the still video is presented on the monitor.

If a mass memory for storing data of a number of video frames is provided in the ultrasonic control unit, the ultrasonic diagnosing apparatus itself becomes bulky and costly. In this embodiment, the video processor unit 152 is provided external to the ultrasonic control unit considering these disadvantages. Since the video processor unit 152 has typically a mass memory for video processing, the mass memory is available for the purpose of this embodiment. Thus, such an existing video processor unit may be taken advantage of.

Figure 23:
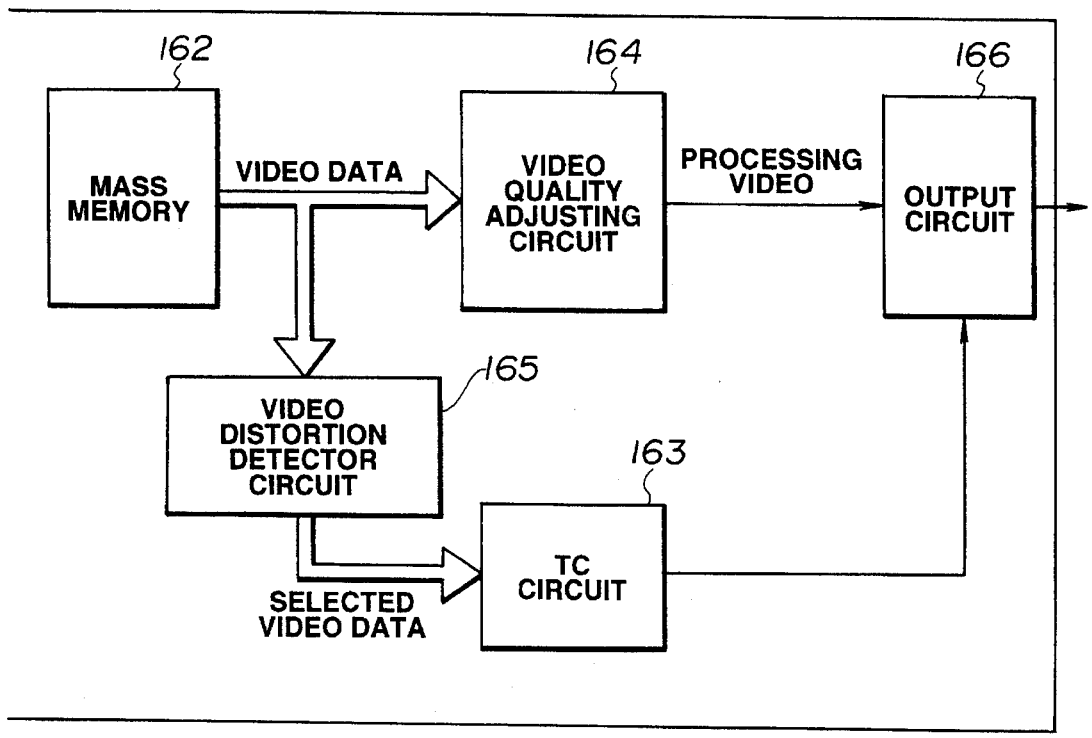
FIG. 23 is a block diagram showing the major portion of the ultrasonic control unit according to embodiment 10 of the present invention.

FIG. 23 shows the video processor unit according to the embodiment 10 of the present invention. The embodiment 10 comprises the video processor unit provided with a video distortion detector circuit for use in tissue texture diagnosing.

As shown in FIG. 23, the video processor unit 161 includes a TC circuit 163 that performs tissue texture diagnosing by analyzing the speckle pattern in the video data stored in a mass memory 162. The TC circuit 163 is not limited to the speckle pattern analysis. It may use histogram and pattern matching technique.

In the video processor unit 161, the video data in the mass memory 162 is sent to a video quality adjusting circuit 164 that adjusts video quality, typically in post-processing, while the video data is also sent to the TC circuit 163 via a video distortion detector circuit 165.

The result of tissue texture diagnosing given by the TC circuit 163 is fed to an output circuit 166, where the result is superimposed on the processed video from the video quality adjusting circuit 164, and then output to the monitor. As a result, the result of tissue texture diagnosing and the processed video are presented in overlay on the monitor.

The advantage of this embodiment is as follows.

In this embodiment, the video distortion detector circuit 165 is disposed in the middle between the mass memory 162 and the TC circuit 163. Thus, only the video frame with the least distortion at 3 o'clock is transferred to the TC circuit 163.

The TC circuit 163 analyzes the speckle pattern in the video data to determine the tissue texture. When texture diagnosing is performed by analyzing the intensity of the video data, the tissue imaged in the video having a discontinuity at 3 o'clock tends to be diagnosed as a tissue different from the normal tissue.

The present invention allows the TC circuit 163 to analyze the video data having no discontinuity at 3 o'clock. The tissue at 3 o'clock is less subject to erroneous diagnosing, and an improved diagnosis reliability results.

Figure 24:
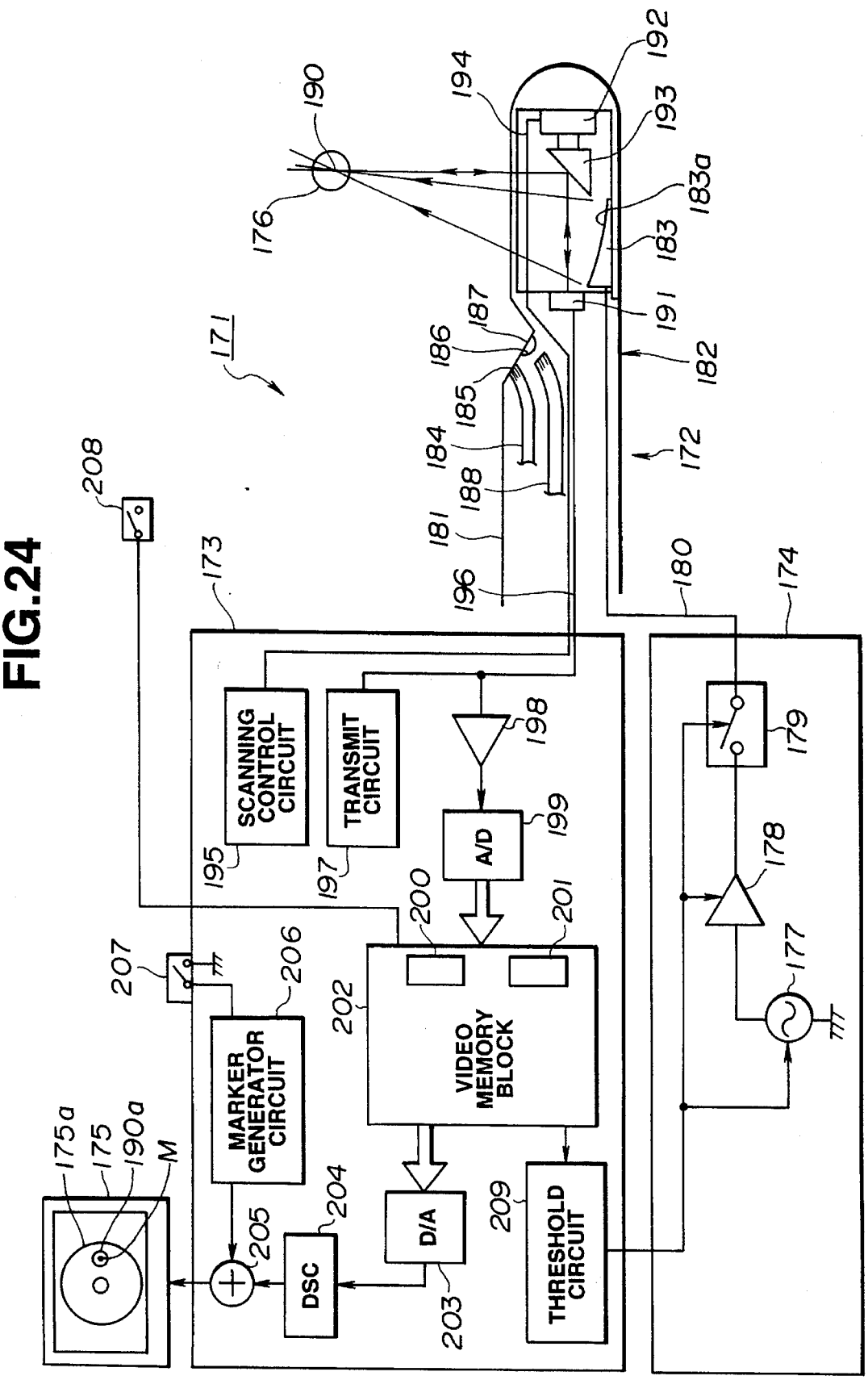

FIG. 24 shows the ultrasonic diagnosing apparatus according to the embodiment 11 of the present invention. The embodiment 11 comprises the ultrasonic control unit having a video distortion detector circuit and an ultrasonic treatment unit for directing a high-powered ultrasonic wave to the tissue of the subject to treat it.

As shown in FIG. 24, the ultrasonic diagnosing apparatus 171 comprises an ultrasonic treatment endoscope 172, an ultrasonic control unit 173, an ultrasonic treatment unit 174, two units of which are connected to the endoscope 172, and a display monitor 175.

When ultrasonic wave is directed to a lesion 176 to treat it, the ultrasonic treatment unit 174 is used in parallel with the ultrasonic control unit 173 for viewing the lesion 176.

The ultrasonic treatment unit 174 comprises a reference high frequency signal source 177 for generating ultrasonic wave for treatment of the lesion 176, a power amplifier 178 for amplifying the reference high frequency signal up to an ultrasonic output power level required for treatment, and a switch 179 for conducting or cutting off the high-tension driving signal output by the power amplifier 178.

The ultrasonic treatment endoscope 172 comprises, on the end portion 182 of an elongated insert assembly 181, optical illumination means, optical viewing means, a treatment transducer 183 for generating a high-powered treatment ultrasonic wave, and acoustic sounding means. The treatment ultrasonic transducer 183 connects to the switch 179 via a driving cable 180.

A light guide 184 as the optical illumination means is passed through the insert assembly 181. The proximal end of the light guide 184 is connected to an unshown light source, from which illumination light is supplied. The light guide 184 guides illumination light to its distal end which is secured to an illumination window 185 in the end portion 182. Illumination light is projected through the window 185 to light forwardly.

Disposed next to the illumination window is a viewing window 186, onto which an objective lens 187 is mounted as the optical viewing means. The objective lens 187 forms the optical image of the illuminated region at the point of focus. Disposed at the point of focus is the distal end of an image guide 188, and the image guide 188 transmits the optical image formed at the distal end to its proximal end. An eye-piece is mounted facing the proximal end of the image guide 188. The operator can view the optical image provided through the eye-piece.

Provided as the acoustic sounding means in the end portion 182 are a transducer 191 for transmitting and receiving sounding ultrasonic wave and the inclined surface of an ultrasonic reflecting mirror 193 that is rotated by a motor 192.

The motor 192 connects to a scanning control circuit 195 in the ultrasonic control unit 173 via a driving cable 194. The scanning control circuit 195 controls the motor 192 so that it rotates at a constant speed.

The transducer 191 connects to a transmit circuit 197 and a receive circuit 198 in the ultrasonic control unit 173 via a cable 196. The transmit circuit 197 feeds a high-frequency pulse signal to the transducer 191 to cause it to generate ultrasonic wave. The receive circuit 198 amplifies the signal received by the transducer 191.

Ultrasonic wave projected in the longitudinal direction (axial direction) of the insert assembly 181 is reflected off the mirror 193 at right angles with respect to the longitudinal direction of the insert assembly 181. Ultrasonic wave thus scans, and is reflected from the region of the subject body. The reflected ultrasonic wave reverses the same route back to the transducer 191.

The ultrasonic treatment transducer 183, having a concave ultrasonic radiating face 183a, directs ultrasonic wave in a manner that the radiating face 183a focuses the treatment ultrasonic wave. As shown in FIG. 24, the treatment ultrasonic wave is designed to have a focus point 190 in the plane in which the sounding ultrasonic wave is scanned.

To this end, the ultrasonic radiating face 183a is formed slightly slant with respect to the longitudinal direction (axial direction) of the insert assembly 181 so that the ultrasonic treatment transducer 183 directs the treatment ultrasonic wave in a slightly slant direction toward the distal end of the assembly rather than in a direct right angle with respect to the longitudinal direction of the assembly. Such an arrangement allows a focus point 190a of the treatment ultrasonic wave to appear at a fixed bearing (to the right of the center of scanning in FIG. 24, namely, at 3 o'clock) and at a fixed range (distance from the center) in an ultrasonic tomographic image display area 175a obtained from the transducer 191 and displayed on the monitor 175.

The end portion 181 is adjusted so that the image of the lesion 176 to be treated appears close to the focus point 190a on the monitor 175 and then the treatment ultrasonic wave is transmitted. Thus, the lesion 176 is subjected to ultrasonic treatment.

The output of the receive circuit 198 is analog-to-digital converted by an A/D converter 199, and fed to a video memory block 202 having a mass memory 200 and a video distortion detector circuit 201. The output of the video memory 202 is digital-to-analog converted by a D/A converter 203, and converted by a DSC (digital-scan converter) 204 into a standard video signal, which is then-fed to an adder 205. The adder 205 superimposes a marker signal from a marker generator circuit 206 onto the standard video signal. The resulting signal is sent to the monitor 175 to be displayed there as an ultrasonic tomographic image.

The marker signal presents a marker M on the display screen to indicate a point of focus 190a to help recognize it easily. A switch 207 is available to display or hide the marker M.

The video memory block 202 is connected to a freeze switch 208 such as a foot-pad switch. When the freeze switch 208 is pressed, the video memory block 202 activates the video distortion detector circuit 201 to perform video distortion detection. The video distortion detector circuit 201 correlates data on the start sounding line and final sounding line (corresponding to the start of drawing and end of drawing of each frame) to determine the degree of distortion of each frame, and outputs a level signal representing the degree of distortion to a threshold circuit 209.

The threshold circuit 209 determines whether or not the degree of distortion is greater than a reference value (threshold value). When the degree of distortion is smaller, the threshold circuit 209 outputs a treatment unit output control signal. The treatment unit output control signal controls amplification and signal level of the reference signal source 177 and power amplifier 178, and switching function of the switch 179.

Figure 25A:
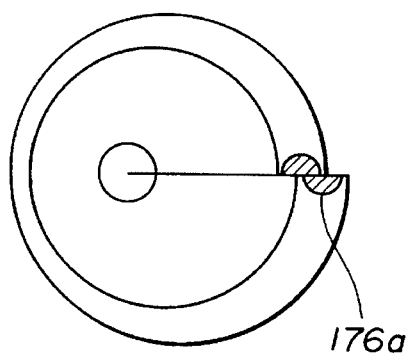
Figure 25B:
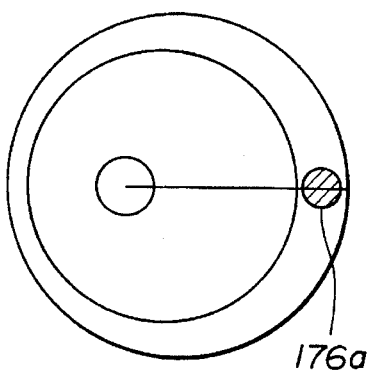

The advantage of this embodiment is discussed referring to FIGS. 25A and 25B.

In the full-circle scanning operation, there is a time difference between the start and end of video drawing. When the image of the lesion appears on the initial sounding line, the video including the image 176a of the lesion 176 suffers a discontinuity as shown in FIG. 25A if the movement of a subject causes a relative displacement between the lesion 176 and the ultrasonic treatment endoscope 172.

When the lesion 176 remains stationary relative to the ultrasonic treatment endoscope 172, the initial sounding line presents no discontinuity as shown in FIG. 25B.

If the initial sounding line at the lesion image is presented and the degree of discontinuity is monitored, the relative positional displacement between the ultrasonic treatment endoscope 172 and the lesion 176 is detected.

In this embodiment, the video distortion detector circuit 201 is disposed along with the mass memory 200 in the video memory block 202 in the sounding ultrasonic control unit 173. The video distortion detector circuit 201 detects a relative displacement of the initial sounding line, and the threshold circuit 209 determines whether the relative displacement is greater than the threshold value. When the relative displacement between the ultrasonic treatment endoscope 172 and the lesion 176 changes greatly and exceeds the threshold value, a treatment output control signal is generated to lower the output of the ultrasonic treatment unit 174.

When this control signal is output, at least, the reference signal source 177, power amplifier 178 and switch 179 are set to lower the ultrasonic output power.

According to this embodiment, when the relative separation between the ultrasonic treatment endoscope 172 and the lesion varies, the output power of the treatment ultrasonic wave is lowered. As a result, energy of the ultrasonic wave that irradiates the region other than the lesion is lowered. Damaging the tissue other than the lesion is thus avoided.

Discussed next is the embodiment 12 of the present invention. The embodiment 12 determines the correlative value (or the degree of coincidence) between data of two sounding lines with one scanning duration apart therebetween and obtains the least distorted video in terms of distortion attributed to the movement of the body.

Figure 26:
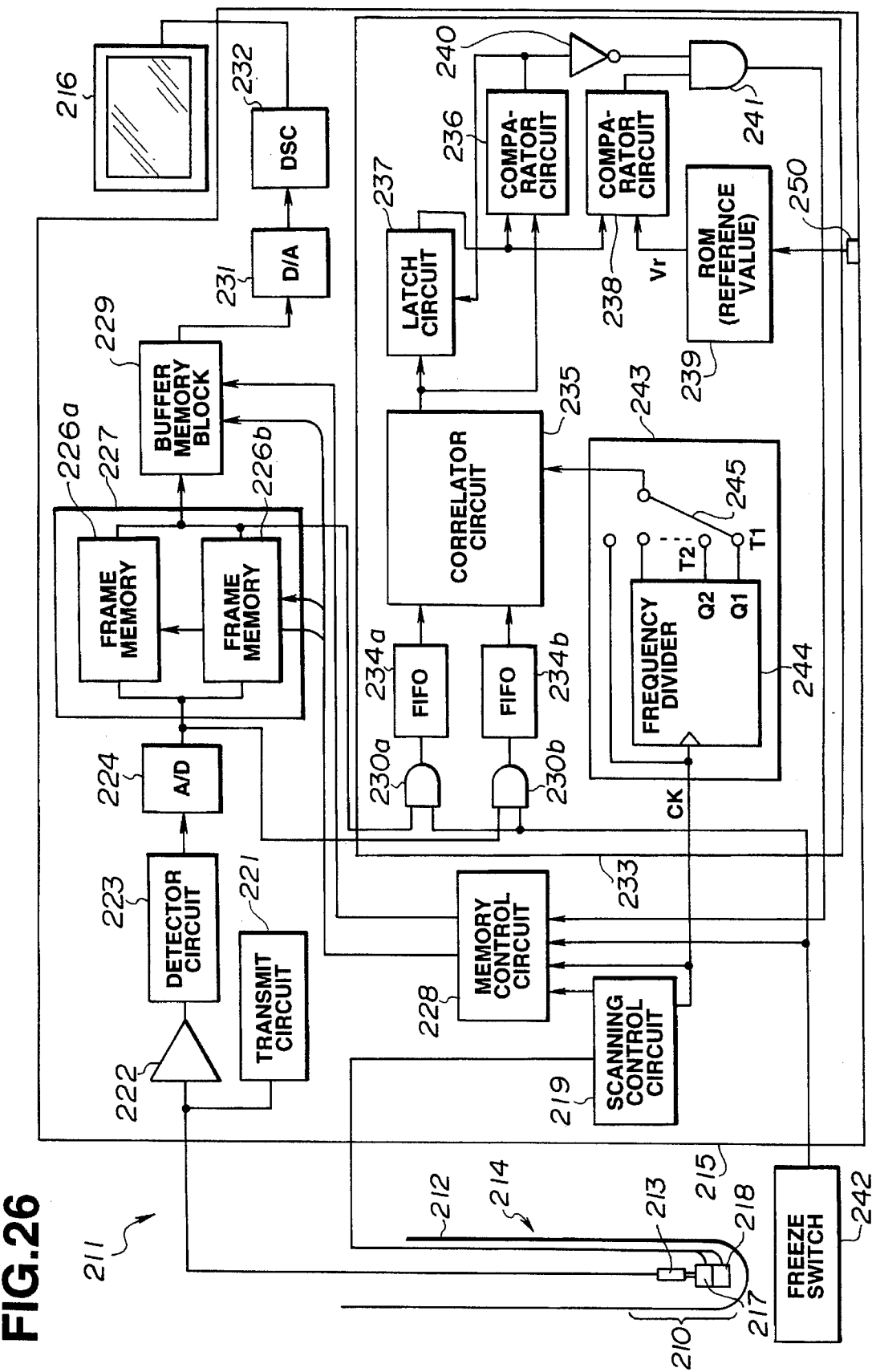

The ultrasonic diagnosing apparatus 211 in FIG. 26 comprises an ultrasonic endoscope 214 having an ultrasonic transducer 213 on the end portion 210 of its long insert assembly (probe) 212, a control unit 215 that performs signal processing to the transducer 213, and a monitor 216 for displaying an ultrasonic image produced in the control unit 215. FIG. 26 does not show optical viewing means.

The transducer 213 is connected to a motor 217. The transducer 213 is rotated by the motor 217 to scan ultrasonic wave. A rotary encoder 218 is mounted on the axis of rotation of the motor 217 to sense the angle of rotation of the motor. The motor 217 and the encoder 218 are connected to a scanning control circuit 219 in the control unit 215. The signal from the encoder 218 is used to control the motor 217 at its constant speed.

The transducer 213 driven by the transmission signal from a transmit circuit 221 is rotated by the motor 217 as scanning means so that ultrasonic wave from the transducer 213 scans the living tissue of the subject.

The ultrasonic echo signal received by the transducer 213 is electro-acoustically converted into an electrical signal, which is then amplified by a receive circuit 222, and then envelope-detected by a detector circuit 223.

The detected signal is digital-to-analog converged by an A/D converter 224, and then written onto a video memory 227 having two frame memories 226a, 226b. A memory control circuit 228 controls read/write operations to the frame memories 226a, 226b.

The video data of a single frame is written onto, and read from, alternately between the two frame memories 226a, 226b. One frame memory onto which the video data is not being written at any moment is being read. The video data of a single frame is written or read for a duration of full-scanning period (namely, one frame period equals to one scanning period).

The video data read from the video memory 227 is input to a buffer memory 229 having a memory capacity of one video frame data. The buffer memory 229 is a dual-port memory. The video data read from the buffer memory 229 is digital-to-analog converted by a D/A converter 231, converted from polar to rectangular coordinate video signal by a DSC circuit 232, and then output to the monitor 216 at a predetermined frame rate.

Data read from the frame memories 226a, 226b on a sounding line basis is fed via an AND gate circuit 230a to a first FIFO memory 234a that constitutes a correlative value detector circuit 233. The output of the A/D converter 224 is fed to a second FIFO memory 230b via an AND gate circuit 230b. Two AND gate circuits 230a, 230b receive a freeze signal as the command signal for a still video presentation by a freeze switch 242. The freeze signal works as a control signal for opening or closing the gating of the two AND gate circuits 230a, 230b.

During the freeze signal ON period, both AND gate circuits 230a, 230b are opened. The second FIFO memory 234b receives the sounding line data that comes one frame period later than the sounding line data that is read from the frame memory 226a or 226b. Each of the two FIFO memories 234a, 234b has a memory capacity of one sounding line data (for example, 512 data).

The outputs of the two FIFO memories 234a, 234b are fed to a correlator circuit (or a coincidence determining circuit) 235 that determines a correlative value (a degree of coincidence). The correlator circuit 235, for example, may be constructed of a comparator that determines data coincidence between two sets of data at each of the bits, the number of which is equal to the number of bits of A/D conversion (or upper bits) of the A/D converter 224. Bits of coincidence are weighted and added for the number of data per sounding line.

For example, suppose that the number of bits of A/D conversion is 8. If a pair of data fully coincide with each other, the degree of coincidence is 256. For the number of data per sounding line (512 data), the degree of coincidence is 256×512 at maximum. If normalized, 256×512 represents a correlative value of 1.

The correlative value calculated by the correlator circuit 235 is stored in an internal latch circuit. The latch circuit holds the data for one clock period. At the rising edge of the next clock, the latch circuit holds a new correlative value.

The correlative value calculated by the correlator 235 is fed to a first comparator circuit 236. The first comparator circuit 236 compares the correlative value with the one stored in the latch circuit 237. The comparator circuit 236 controls storing the correlative value to the latch circuit 237.

Namely, the comparator circuit 236 compares a new correlative value output by the correlator circuit 235 with the correlative value (comparative value) stored in the latch circuit 237. When the new correlative value is greater, it is stored in the latch circuit 237 as a comparative value.

The output of the latch circuit 237 is fed to a second comparator circuit 238, where the output of the latch circuit 237 is compared with a correlative reference value (reference value) Vr stored in a ROM 239. This reference value is approximately 1. If the correlative value is greater than the reference value, the movement of the body relative to the end portion 210 or the movement of the end portion 210 relative to the body is marginally small or almost zero. The reference value Vr is set by a selection switch 250.

The output of the first comparator circuit 236 is inverted by an inverter 240. The output of the second comparator circuit 238, along with the inverted signal from the inverter 240, is fed to a memory control circuit 228 via an AND gate circuit 241 as a timing signal for determining a still video. Namely, the AND gate circuit 241 outputs the timing signal when the provided correlative value is greater than the reference value and when the correlative value that is provided later tends to drop (in other words, the correlative value is at maximum).

The freeze switch 242 feeds a freeze signal or an unfreeze signal to the memory control circuit 228. When the timing signal comes in from the AND gate circuit 241 with the freeze switch 242 on, the memory control circuit 228 outputs a write disable signal to the buffer memory 229 at the rising edge of the timing signal, thereby locking the video data that has been written onto the buffer memory 229 immediately before the timing signal. The freeze signal is also fed to the correlator circuit 235, which calculates correlative value only while the freeze signal is entered.

In this embodiment, the period of correlative value calculation is selected as follows. The clock CK of the sounding line period provided by the scanning control circuit 219 is fed to a frequency divider circuit 244 constructed of a counter or the like in a period setting circuit 243. A selector switch 245 selects the clock CK or any of clocks which are frequency divided by the frequency divider 244. The selected clock is fed to (the latch of) the correlator circuit 235.

A terminal Q1, for example, gives the clock that is frequency-divided in the maximum division ratio, and its period T1 agrees with a scan period Ts. Another terminal Q2 offers the clock whose period is half the period T1. The remaining terminals give shorter periods. The operator selects any one from these periods.

The clock CK of the sounding line period output from the scanning control circuit 219 and the Z-phase signal output per rotation or scan are fed to the memory control circuit 228. The memory control circuit 228 performs data writing to and data retrieval from the video memory 227 in synchronism with these clocks.

The operation of the embodiment 12 is further discussed referring to FIGS. 27A through 27L. In the normal motion-video mode (with the freeze switch 242 off), after being processed through the receive circuit 222, detector circuit 223 and A/D converter 224, the received signal is written onto one of the frame memories, 226a, of the video memory 227 in the form of time-series sounding line data A0, A1, . . . , An (FIG. 27A) obtained for one scanning duration Ts (one scanning period), where n is 511, for example.

For the next scanning duration Ts, the sounding line data B0, B1, . . . , Bn (FIG. 27B) are sequentially written onto the other frame memory 226b. At the same time, the sounding line data (FIG. 27A) is sequentially read from the frame memory 226a and written onto the buffer memory 229 (FIG. 27C). In FIGS. 27A, 27B, 27C, the sounding line data Ai, Bi, Ci, Di, . . . represent the same sounding line data i (i=0, . . . ,n) on time-series in steps of time difference of one scanning duration Ts with Ai being earliest.

The sounding line data is written onto the buffer memory 229 sequentially in time-series as shown in FIG. 27C (new sounding line data overwrites old one). The buffer memory 229 allows write operation and read operation to be performed in parallel. The resulting video data read from the buffer memory 229 is output via the D/A converter 231 and DSC circuit 232 to the monitor 216, where a motion-video is presented.

When the operator turns on the freeze switch 242 at the timing shown in FIG. 27J during motion-video presentation, a freeze signal is fed to the memory control circuit 228. The memory control circuit 228 is ready to receive the output from the AND gate circuit 241. Also, the freeze signal opens the AND gate circuits 230a, 230b. The correlator circuit 235 is ready to calculate a correlative value.

Each of the sounding line data Mi (M=C, D, . . . ) that is read from the frame memory 226a after the freeze ON or trigger signal is sequentially stored in the FIFO memory 234a. On the other hand, the other FIFO memory 234b stores the corresponding sounding line data Ni (N=D, E, . . . ) that is one frame period late.

The period setting circuit 243 is set to the maximum period T1, for example. As shown in FIG. 27D, correlative value is calculated at the first timing of each scanning duration after the freeze trigger signal. Calculated correlative values are Vcd, Vde, Vefd, . . . as shown in FIG. 27E. The correlative value Vcd, for example, represents the correlative value between the sounding line data C0 and D0. The correlative value changes with time as in FIG. 27E.

The first comparator 236 compares the first correlative value Vcd with the comparative value in the latch circuit 237. Since Vcd>0, the correlative value Vcd is stored in the latch circuit 237 as a comparative value. One scanning duration later, the correlative value Vde is compared with the comparative value Vcd. Since Vde>Vcd, the correlative value Vde is stored in the latch circuit 237 as a comparative value.

The comparative value in the latch circuit 237 changes as shown in FIG. 27F. The reference value Vr stored in the ROM 239 is represented by the broken line in FIG. 27E. The second comparator circuit 238 is driven high at the timing the comparative value Vef is stored in the latch circuit 237 (FIG. 27H).

The first comparator circuit 236 is driven low at the moment the next comparison in succession to the maximum correlative value of Vfg reveals Vgh<Vfg (FIG. 27G). The low signal from the first comparator circuit 236 is inverted by the inverter 240 into a high signal, which is fed to the AND gate circuit 241. The AND gate circuit 241 also receives the high signal from the second comparator circuit 238. The AND gate circuit 241 thus gives the timing signal to the memory control circuit 218.

Upon receiving the timing signal, the memory control circuit 218 outputs the write disable signal to the buffer memory 229, holding the video data that was written immediately before the write disable signal. Specifically, video data F0, ..., Fn immediately before video data G0, ..., Gn was written are held (Strictly speaking, F0 of video data F0, ..., Fn is replaced with G0. To avoid this, a delay circuit for presenting a delay of one sounding line may be placed in front of the buffer memory 229.)

With the scanning duration as its period, the buffer memory 229 holds the video that offers the maximum correlative value, namely, the video that is least distorted by the displacement of the body or the endoscope 214. This video is presented on the monitor 216 as a still video.

In the above discussion, the period of correlative value determination is one scanning duration Ts. If half the period Ts, namely, T2, is used, the frequency of correlative value determination is doubled as shown in FIG. 27K. Correlative value is determined in the middle of two timings of determination of FIG. 27D.

In this case, the AND gate circuit 241 gives the timing signal as shown in FIG. 27L. The correlative value is at maximum at Vfg. With the scanning duration Ts, the determination of the maximum correlative value must wait until comparison with another correlative value one scanning duration Ts later. If a shorter period (in this case, half the period Ts, namely T2) is used, the maximum correlative value is determined within a shorter time. The timing signal is given at a faster timing. In this case, the buffer memory 229 has video data, with E in half and F in half.

When correlative value determination is performed at the period T2, the video of the maximum correlative value is locked at half the scanning duration and displayed on the monitor 216 as a still video. If a shorter period is used, the video having the maximum correlative value is obtained shorter time.

According to the embodiment 12, the video having the maximum correlative value is locked and then displayed on the monitor 216 as a still video.

This embodiment has been discussed with reference to the full-circle scanning system. Since correlative value determination is performed between data on two sounding lines with one scanning duration apart therebetween, the same technique is applied to a sector or linear scanning system. According to this embodiment, no large video memory is required and a least distorted still video is easily obtained.

When scanning durations of 10 frames or more are required to reach the reference value after an instruction of freeze operation, a sufficiently least distorted still video is obtained by using the pair of frame memories 226a, 226b and the buffer memory 229 as video memories.

According to the embodiment 12, the still video least distorted and sufficient enough to reach the reference value Vr is assuredly obtained regardless of the memory capacity of the video memory. The operator is allowed to select the value of the reference value Vr (by the selection switch 250) for a better quality image to his satisfaction.

A correlative value between a pair of sounding line data is determined over a scanning duration, and thus the degree of distortion of a frame over the scanning duration is calculated. The degree of distortion is determined in a short time. The determination of the correlative value between the pair of sounding line data may be performed using part of these data.

In the construction shown in FIG. 26, the inverted output of the first comparator circuit 236 and the output of the second comparator circuit 238 are AND-gated into the timing signal that is fed to the memory control signal 228. Alternatively, the output of the second comparator circuit 238 is fed to the memory control circuit 228 as its timing signal. In this case, the least distorted video is held and output as a still video.

Any combination of the above embodiments, in whole or in part, falls within the scope of the present invention. For example, when the freeze switch 10 is operated in the embodiment 1, the scanning means (the rotation of the motor 71) is stopped after determining whether or not the degree of distortion of a video frame is greater than the reference value and outputting the video as a still video when the degree of distortion is smaller than the reference value, rather than immediate stopping of the scanning means. Furthermore, when the determination reveals that the degree of distortion is smaller than the reference value, any video frame of which degree of distortion is the least may be output as a still video.

The present invention is not limited to the above, and includes modifications or embodiments derived from or a combination of the aboveembodiments and alternate examples.

What is claimed is:

1. An ultrasonic diagnosing apparatus comprising:

ultrasonic generator means including an ultrasonic transducer for feeding a driving signal to said ultrasonic transducer to generate ultrasonic wave;

scanning means for causing the ultrasonic wave generated by said ultrasonic transducer to scan a predetermined scanning region for a predetermined scanning duration;

video data memory means for storing returned signals, which are received and electro-acoustically converted by said ultrasonic transducer, in a plurality of video frames of video data obtained over a plurality of predetermined scanning durations, video frame by video frame, each video frame corresponding to said scanning region;

video distortion detector means for detecting the degree of distortion in the video in each of said video frames stored in said video data memory means;

video selector control means for performing selection control so that said video data memory means outputs selectively the video of a video frame that is found to suffer less degree of distortion based on said degree of distortion detected by said video distortion detector means; and video display means for presenting said video of said video frame selected by said video selector control means.

2. The ultrasonic diagnosing apparatus according to claim 1, wherein said video distortion detector means detects the video frame of video data having the least degree of distortion among said plurality of video frames of video data stored in the said video data memory means.

3. The ultrasonic diagnosing apparatus according to claim 1, wherein said ultrasonic transducer is mounted on the end of an elongated probe.

4. The ultrasonic diagnosing apparatus according to claim 1, wherein said video distortion detector means comprises coincidence determining means that detects the degree of coincidence between the video data at the start of scanning and the video data at the end of scanning in each of said video frames of video data stored in said video data memory means and determines the video data having a larger degree of coincidence as the video data of less distortion.

5. The ultrasonic diagnosing apparatus according to claim 1, wherein said video distortion detector means determines said degree of distortion of video, whereby the timing of the peak value of video data is used to detect a discontinuity between the start of scanning and end of scanning.

6. The ultrasonic diagnosing apparatus according to claim 1 further comprising Doppler frequency detector means for detecting a Doppler shift of the received ultrasonic frequency relative to a transmitted ultrasonic frequency, and Doppler video memory means for storing a plurality of video frames of video data having Doppler shifted frequency from said Doppler frequency detector means, whereby said video selector control means outputs to said video display means as a quasi-color signal a Doppler video in phase with the video frame of video data selectively output by said video data memory means.

7. The ultrasonic diagnosing apparatus according claim 1, wherein said scanning means is mechanical scanning means for causing the ultrasonic wave transmitted from said ultrasonic transducer to mechanically scan.

8. The ultrasonic diagnosing apparatus according claim 1, wherein said ultrasonic generator means comprises an ultrasonic transducer array constructed of a plurality of ultrasonic transducers, and said scanning means is electronic scanning means for electronically driving said ultrasonic transducer array to scan a region of scanning.

9. The ultrasonic diagnosing apparatus according claim 1, wherein said scanning means causes the ultrasonic wave transmitted from said ultrasonic transducer to scan in a full circle.

10. The ultrasonic diagnosing apparatus according claim 1 further comprising video selector means for outputting to said video display means sequentially in time-series the plurality of video frames of video data stored in said video data memory means.

11. The ultrasonic diagnosing apparatus according claim 1, wherein said ultrasonic generator means comprises a transmit circuit for applying a driving signal to said ultrasonic transducer for said ultrasonic transducer to vibrate ultrasonically.

12. The ultrasonic diagnosing apparatus according claim 1 further comprising a ultrasonic treatment transducer for transmitting a treatment ultrasonic wave.

13. The ultrasonic diagnosing apparatus according claim 1, wherein said ultrasonic transducer is mounted on the end of an elongated probe, and said end of the probe is provided with optical illumination means and optical viewing means for optical illumination and viewing, respectively.

14. The ultrasonic diagnosing apparatus according claim 1, wherein said ultrasonic generator means comprises an ultrasonic endoscope having said ultrasonic transducer on the end of an elongated probe and optical illumination means and optical viewing means for optical illumination and viewing, respectively.

15. The ultrasonic diagnosing apparatus according claim 1 further comprising freeze command means for commanding a still video presentation to said video display means.

16. The ultrasonic diagnosing apparatus according claim 15, wherein said video distortion detector means detects the least distorted video frame of video data from said plurality of video frames of video data stored in said video data memory means when said freeze command means commands a still video presentation.

17. An ultrasonic diagnosing apparatus comprising:

ultrasonic transmit and receive means for causing an ultrasonic transducer to transmit ultrasonic wave in a scanning manner and to receive returned ultrasonic wave;

scanning means for causing the ultrasonic wave transmitted from said ultrasonic transducer to scan a predetermined scanning region for a predetermined scanning duration;

video data memory means for storing a plurality of video frames of video data, each video frame of video data obtained closely in time but in different scanning durations through transmission and reception of said ultrasonic wave;

freeze command means for commanding a freeze operation of a still video presentation;

video distortion detector means for detecting the degree of distortion of each of the plurality of video frames of video data, prior to the freeze command, stored in said video data memory means when said freeze command means issues the freeze command; and display control means for selectively displaying the video frame of video data in still video based on the result of detection by said video distortion detector means.

18. The ultrasonic diagnosing apparatus according to claim 17, wherein said video distortion detector means comprises coincidence determining means that detects the degree of coincidence between the video data at the start of scanning and the video data at the end of scanning in each of the video frames of video data stored in said video data memory means and determines the video data having a larger degree of coincidence as the video data of less distortion.

19. An ultrasonic diagnosing and treatment system comprising an ultrasonic diagnosing apparatus comprising:

ultrasonic transmit and receive means for causing an ultrasonic transducer to transmit ultrasonic wave and to receive returned ultrasonic wave, scanning means for causing the ultrasonic wave transmitted from said ultrasonic transducer to scan a predetermined scanning region for a predetermined scanning duration, video data memory means for storing a plurality of video frames of video data, each video frame of video data obtained close but different times through transmission and reception of said ultrasonic wave, and video distortion detector means for detecting the degree of distortion of each of the plurality of video frames of video data stored in said video data memory means; and a treatment unit comprising:
  treatment ultrasonic irradiation means for focusing ultrasonic energy to irradiate a lesion, and
  energy control means for controlling the level of ultrasonic energy in response to the control signal from said output means.

20. The ultrasonic diagnosing and treatment system according to claim 19, wherein said video distortion detector means comprises coincidence determining means that detects the degree of coincidence between the video data at the start of scanning and the video data at the end of scanning in each of the video frames of video data stored in the said video data memory means and determines the video data having a larger degree of coincidence as the video data of less distortion.

21. An ultrasonic diagnosing apparatus comprising:
  ultrasonic generator means, including an ultrasonic transducer for feeding a driving signal to said ultrasonic transducer to generate ultrasonic wave;
  scanning means for causing the ultrasonic wave generated by said ultrasonic transducer to scan a predetermined scanning region for a predetermined scanning duration;
  video data memory means for storing returned signals, which are received and electro-acoustically converted by said ultrasonic transducer, as video data obtained over a plurality of predetermined scanning durations;
  correlator means for detecting a correlative value between two sets of data of two identical sounding lines but with one scanning duration apart in time therebetween in said video data;
  video selector control means for determining whether the correlative value detected by said correlator means is equal to or greater than a predetermined value, and for selectively outputting from said video memory means the video corresponding to the correlative value that is found to be equal to or greater than the predetermined value; and
  video display means for presenting the video selected by said video selector control means.

22. The ultrasonic diagnosing apparatus according to claim 21, wherein said video selector control means for selectively outputting from said video data memory means the video corresponding to the correlative value when said correlative value detected by said correlator means is equal to or greater than said predetermined value and when the correlative value detected by said correlator means is greater than a second correlative value that is detected later.

23. The ultrasonic diagnosing apparatus according to claim 21, wherein said ultrasonic transducer is mounted on the end of an elongated probe.

24. The ultrasonic diagnosing apparatus according claim 21, wherein said scanning means is mechanical scanning means for causing the ultrasonic wave transmitted from said ultrasonic transducer to mechanically scan.

25. The ultrasonic diagnosing apparatus according claim 21, wherein said scanning means causes the ultrasonic wave transmitted from said ultrasonic transducer to scans in a full-circle.

26. The ultrasonic diagnosing apparatus according claim 21 further comprising freeze command means for commanding a still video presentation to said video display means.

27. The ultrasonic diagnosing apparatus according claim 26, wherein said correlator means determines at a predetermined period a correlative value between two data sets of two sounding lines with one scanning duration apart therebetween in the plurality of video data obtained in time-series, and said video selector control means outputs to said video display means the video data having the same timing at the moment the correlative value obtained per said predetermined period and in time-series is maximum.

28. The ultrasonic diagnosing apparatus according claim 27 further comprising means for setting a variable time for said predetermined period for determining said correlative value.

29. The ultrasonic diagnosing apparatus according claim 21, wherein a variable value is set for said predetermined value.

* * * * *